United States Patent
Zak

(10) Patent No.: US 11,544,756 B2
(45) Date of Patent: *Jan. 3, 2023

(54) WEB SERVICE METHOD

(71) Applicant: Bruce Zak, Oxford, MI (US)

(72) Inventor: Bruce Zak, Oxford, MI (US)

( * ) Notice: Subject to any disclaimer, the term of this patent is extended or adjusted under 35 U.S.C. 154(b) by 248 days.

This patent is subject to a terminal disclaimer.

(21) Appl. No.: 16/910,075

(22) Filed: Jun. 24, 2020

(65) Prior Publication Data

US 2020/0320602 A1    Oct. 8, 2020

Related U.S. Application Data

(63) Continuation-in-part of application No. 15/453,358, filed on Mar. 8, 2017, now Pat. No. 10,699,325.

(Continued)

(51) Int. Cl.
*G06Q 30/06*    (2012.01)
*A61B 17/20*    (2006.01)
(Continued)

(52) U.S. Cl.
CPC ..... *G06Q 30/0621* (2013.01); *G06Q 30/0623* (2013.01); *G06Q 30/0641* (2013.01);
(Continued)

(58) Field of Classification Search
CPC . G06Q 30/0601–0645; G06Q 30/0621; G06Q 30/0623; G06Q 30/0641;
(Continued)

(56) References Cited

U.S. PATENT DOCUMENTS 6,016,478 A    1/2000 Zhang et al.
6,457,045 B1    9/2002 Hanson et al.
(Continued)

FOREIGN PATENT DOCUMENTS

WO    2001031553 A1    5/2001
WO    2015017836 A2    2/2015

OTHER PUBLICATIONS

Univ beijing posts & telecomm files Chinese patent application for distributed knowledge data mining device and mining method used for complex network. (Oct. 12, 2013). Global IP News.Information Technology Patent News Retrieved from https://dialog.proquest.com/professional/docview/ (Year: 2013).*

(Continued)

*Primary Examiner* — Allison G Wood
*Assistant Examiner* — Ashley D Preston
(74) *Attorney, Agent, or Firm* — Device Patent LLC

(57) ABSTRACT

Disclosed herein is a web service system and method comprising a determine best result engine useful for presenting intelligent objective decisions for at least one scenario for at least one collection of criteria across many different industries and market segments including but not limited to healthcare, manufacturing, and financial services. In some forms, the web service system also or alternatively provides automatic configuration of at least one of an array of items and services and results that a customer/user requires in preparation of completing a task. The web service system can utilize a plurality of knowledge data engines to capture and analyze information of a predetermined type to produce knowledge data for consideration by the determine best result engine.

22 Claims, 26 Drawing Sheets

Related U.S. Application Data

(60) Provisional application No. 62/305,000, filed on Mar. 8, 2016.

(51) Int. Cl.
  *G06Q 50/00* (2012.01)
  *G06Q 40/06* (2012.01)
  *G06Q 10/06* (2012.01)
  *G06Q 10/08* (2012.01)

(52) U.S. Cl.
  CPC ........ *A61B 17/20* (2013.01); *G06Q 10/06395* (2013.01); *G06Q 10/087* (2013.01); *G06Q 40/06* (2013.01); *G06Q 50/01* (2013.01)

(58) Field of Classification Search
  CPC ........... G06Q 10/06395; G06Q 10/087; G06Q 40/06; G06Q 50/01; G06Q 30/0282; A61B 17/20; G06N 5/022; G16H 10/20; G16H 40/20
  See application file for complete search history.

(56) References Cited

U.S. PATENT DOCUMENTS

| | | | |
|---|---|---|---|
| 7,472,170 B2 | 12/2008 | Zak et al. | |
| 8,515,829 B1 | 8/2013 | Conway et al. | |
| 8,713,134 B2 | 4/2014 | Zak et al. | |
| 9,141,720 B2 | 9/2015 | Zak et al. | |
| 9,213,996 B2 | 12/2015 | Pavlidis et al. | |
| 9,483,803 B2 | 11/2016 | Raina et al. | |
| 2002/0178041 A1 | 11/2002 | Krantz et al. | |
| 2003/0040946 A1* | 2/2003 | Sprenger | G06Q 30/06 705/6 |
| 2006/0122899 A1 | 6/2006 | Lee et al. | |
| 2007/0033098 A1 | 2/2007 | Peters et al. | |
| 2007/0150397 A1* | 6/2007 | Rossen | G06Q 40/06 705/36 R |
| 2007/0299777 A1 | 12/2007 | Shraim et al. | |
| 2008/0047851 A1 | 2/2008 | Smit et al. | |
| 2008/0076554 A1* | 3/2008 | Govoni | G06Q 30/0254 463/31 |
| 2008/0183653 A1* | 7/2008 | Byrnes | G06N 5/02 706/50 |
| 2008/0235084 A1 | 9/2008 | Quoc et al. | |
| 2009/0055488 A1 | 2/2009 | Berry et al. | |
| 2009/0055513 A1 | 2/2009 | Berry et al. | |
| 2009/0132665 A1 | 5/2009 | Thomsen et al. | |
| 2009/0281890 A1 | 11/2009 | Aliabadi et al. | |
| 2009/0281927 A1 | 11/2009 | Aliabadi et al. | |
| 2009/0313550 A1 | 12/2009 | Kim et al. | |
| 2010/0124534 A1* | 5/2010 | Harrop | G01N 33/57438 424/9.2 |
| 2011/0282764 A1 | 11/2011 | Borst et al. | |
| 2012/0136689 A1 | 5/2012 | Ickman et al. | |
| 2013/0024291 A1 | 1/2013 | Aliabadi et al. | |
| 2014/0114774 A1 | 4/2014 | Schultz et al. | |
| 2015/0134797 A1 | 5/2015 | Theimer et al. | |
| 2015/0199752 A1 | 7/2015 | Sherman | |
| 2015/0294222 A1 | 10/2015 | Toon et al. | |
| 2020/0321123 A1* | 10/2020 | Neumann | G16H 20/60 |

OTHER PUBLICATIONS

Party in a box. Published Feb. 18, 2016.www.birthdayinabox.com/partythemes/all-parties/star-wars-party.html.

\* cited by examiner

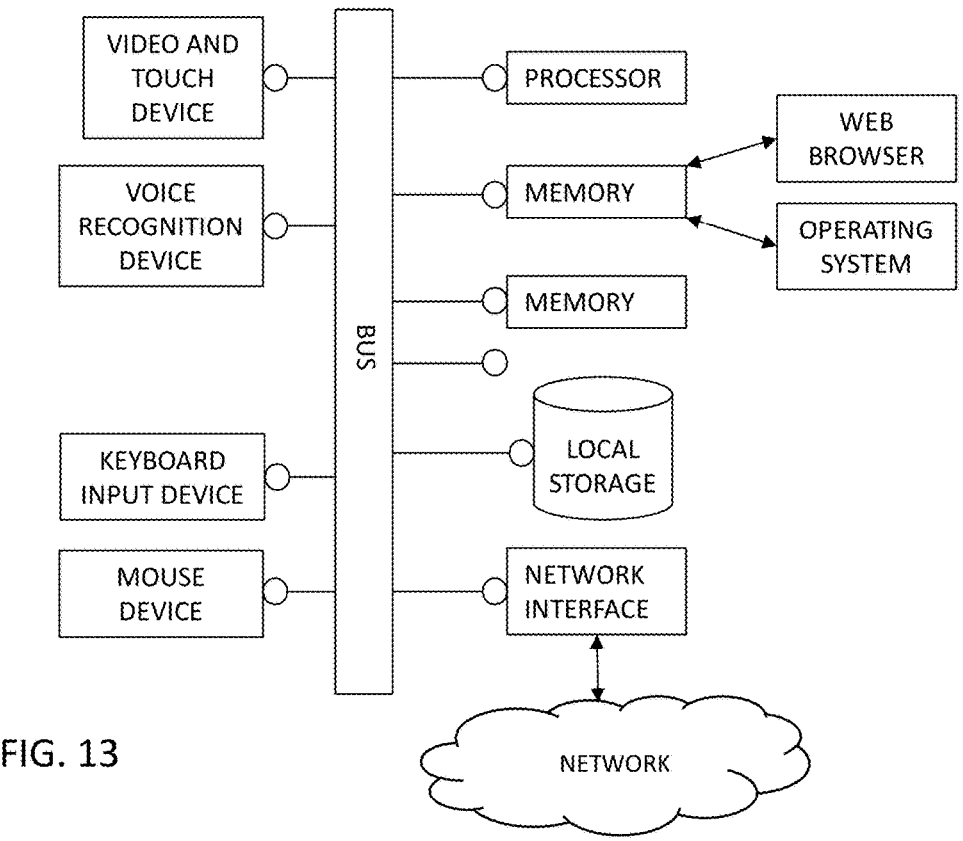
FIG. 13
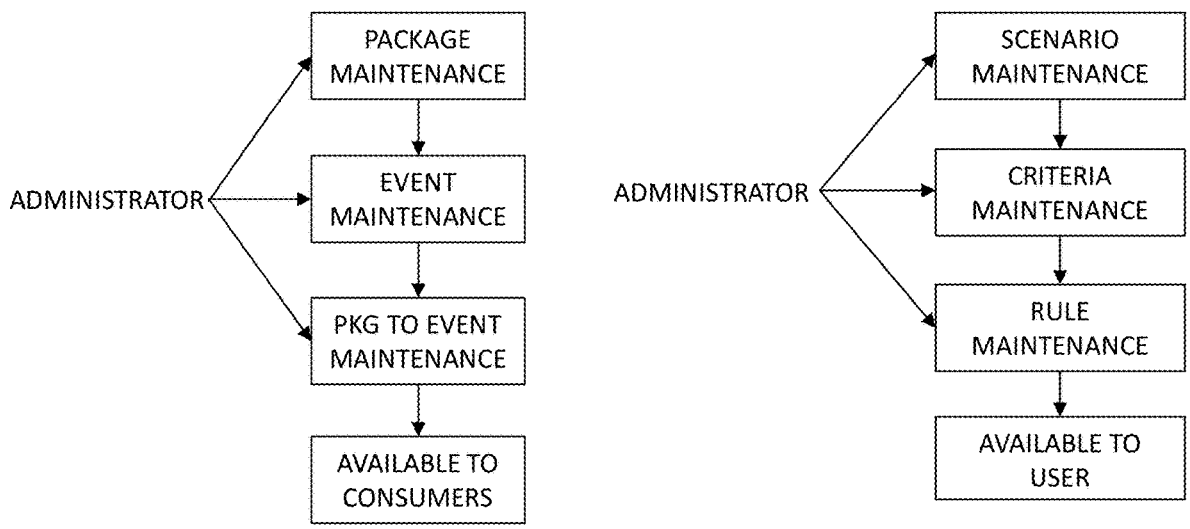
FIG. 14
FIG. 14B

Add A Package

Package Id: 1 (read-only)
Package Name: 
Package Attributes:
Start Date: 
End Date: 
Status:

ok  Cancel

FIG. 15

Package Maintenance

Available Packages: 
or
Package Search: *    go  del  Edit
Package Name:

Search Items: *    go

Selected Package Items        Available Package Items

>>
<< ok  Cancel

FIG. 16

Add A Event

Event Id: 1 (read-only)

Event Name:

Event Attributes:

Start Date:

End Date:

Status:

ok Cancel

FIG. 17

Package(s) to Event Linking

Available Events: 
or
Event Search: * go

Event Name:

Search Packages: * go

Assigned Packages        Available Packages

>>
<< ok Cancel

FIG. 18

|  | PACKAGE | PRODUCT | EVENT | THEME | COLOR | KNOWLEDGE ENGINES |
|---|---|---|---|---|---|---|
| ONLINE COMMERCE: | | | | | | |
| | Grouping of graduation products | Banner | Graduation | Size of party | Black and gold | Social Media |
| | | Centerpieces | | | | Search Results |
| | | Balloons | | | | Inventory Availability |
| | | | | | | Product Satisfaction |
|  | SCENARIO | ELEMENT | CRITERIA | RULE | RULE | KNOWLEDGE ENGINES |
| MANUFACTURING: | | | | | | |
| M1 | Grouping-Quality results from set of machines. | Machine A | Date: 01/10/2020 | Min. 1000 operations/hr. | Greater than equal to 0 | Messaging |
| | | Machine B | | | Less than .17 | Diagnostics |
| | | Machine C | | | | Quality Assurance |
| M2 | Grouping-Quality results from set of machines. | Machine D | Date: 01/10/2020 | Greater than equal to 0 Less than .17 | No dependencies on M1 | Messaging |
| | | Machine E | | | | Diagnostics |
| | | Machine F | | | | Quality Assurance |
| HEALTHCARE: | | | | | | |
| H1 | Grouping-Vaccine candidates. | Trial Vaccine A | Trial period 03/01/20 to 6/30/20 | | | Streaming |
| | | Trial Vaccine B | | | | Messaging |
| | | Trial Vaccine C | | | | Product Satisfaction |
| H2 | Grouping-Test patient candidates. | Patient Trial Group A | Pos. Reaction Type | Exclude top 3% | Linked to Vaccine A | Streaming |
| | | Patient Trial Group B | | | Linked to Vaccine A | Diagnostics |
| | | Patient Trial Group C | | | Linked to Vaccine A | Quality Assurance |
| | | | | | | Messaging |
| H3 | Grouping-Test patient candidates. | Patient Trial Group A | Neg. Reaction Type | Exclude bottom 3% | Linked to Vaccine B | Streaming |
| | | Patient Trial Group B | | | Linked to Vaccine B | Diagnostics |
| | | Patient Trial Group C | | | Linked to Vaccine B | Quality Assurance |
| | | | | | | Messaging |
| FINANCIAL: | | | | | | |
| F1 | Grouping-"Green" stocks. | Stock A | Month over month analysis | Greater than 5% ROI | No relationship with "traditional" energy stocks. | Financial Services |
| | | Stock B | | | | Messaging |
| | | Stock C | | | | Social Media |
| | | | | | | Search Results |
| F2 | Grouping-"Green" stocks. | Stock D | Month over month analysis | Greater than 5% loss | No relationship w/F1 scenario | Financial Services |
| | | Stock E | | | | Messaging |
| | | Stock F | | | | Social Media |
| | | | | | | Search Results |

FIG. 19C

Event Details

Number of Attendees: _____
Number of Tables: _____
Size of Tables: _____
Shape of Tables: _____
Other Criteria 1: _____
Other Criteria 2: _____
Other Criteria 3: _____

Prev << Next >>  Clear  Save  Cancel

FIG. 23

Recommended Package and Results

Recommended Package Items:

| | | Featured Images Here | | |

Inputs:
# of Attendees: _____
# of Tables: _____
Size of Tables: _____
Shape of Tables: _____
Other Criteria 1: _____
Other Criteria 2: _____
Other Criteria 3: _____

Results:
# of Attendees: _____
Total Price: _____
Price per Attendee: _____

Price Guarantee

Buy Now

Prev << Next >>  Clear  Save  Cancel

FIG. 24

WEB SERVICE METHOD

CROSS REFERENCE TO RELATED APPLICATIONS

This is a U.S. Continuation-In-Part Patent Application claiming priority to U.S. Non-Provisional application Ser. No. 15/453,358 filed Mar. 8, 2017 which claims the benefit of U.S. Provisional Patent Application No. 62/305,000 filed Mar. 8, 2016, the entire disclosure of which is hereby incorporated by reference and relied upon.

BACKGROUND OF THE INVENTION

Field of the Invention

The invention relates generally to online commerce systems operating within one or more computing devices. The invention is more particularly related to online commerce systems operating within one or more computing devices that suggest and provide a user an optimal collection of one or more of: goods, services, and results for purchase (GSR).

Description of Related Art

The internet is stocked with numerous suppliers of goods and services and results that are available to consumers. When confronted with a particular task requiring GSR, consumers and business purchasers are typically challenged with task planning, organizing, and shopping across many vendors to find and collect products or services needed to complete a particular task.

For example, the prior art includes online commerce sites such as those operated by Evite® and Punchbowl® that are configured to assist users in organizing an invitation list for an event and offer services for sending invites and thank you notes. However, the process of planning an event extends well beyond an invitation list. What is needed are improved computerized world wide web systems for planning events and for providing customers (which includes consumers and business purchasers) targeted collections of one or more of: goods and services and results needed to simplify execution of an event or accomplish a task.

Current filtering metaphors utilized on the internet today typically create a condition known as information overload. Current metaphors are generally insufficient in an environment of changing form factors and interfaces for mobile devices, tablets and digital devices. They are also insufficient to respond to the constant need for improved efficiency in user's daily lives. What is needed is intelligent internet data processing that helps to streamline non-pertinent options and details regarding products and services and results available from the internet for the benefit of a consumer. What is needed is intelligent internet data processing that has improved objective decision making processes. Intelligent internet data processing will help prevent for example, an engineer choosing a part supplier for subjective reasons such in response to advertising or corporate sponsorships rather than objective reasons such as part quality, timeliness, and price.

SUMMARY OF THE INVENTION

Disclosed herein is a web service system comprising a determine best result engine useful for presenting intelligent objective decisions for at least one scenario for at least one collection of criteria across many different industries and market segments including but not limited to healthcare, manufacturing, and financial services. In some forms, the web service system also or alternatively provides automatic configuration of at least one of an array of items and services and results that a customer/user requires in preparation of completing a task.

Definitions:

Activity: A specific deed, action or function.

Administrator: A person who determines the site policies, business processes and manages the technical operation of an interactive website.

Agnostic: A computing program compatible with a wide range of computing devices and computer operating systems.

App: The abbreviation for a computer application.

Applications: The software programs used by one or more computing devices.

Automatic configuration of an array of items needed for planned event: The automated process of selecting items that would be used for a scheduled activity.

Availability: Readily obtainable; accessible.

Bus: In computer architecture, a bus is a communication system that transfers data between components inside a computer, or between computers.

Client system: The hardware and software programs on a computing device that enable a user to interact with the Web Service System.

Commerce systems: Commerce is the activity of buying and selling of goods and services and results, especially on a large scale. The system can include legal, economic, political, social, and cultural aspects managed by interacting components.

Computer processor: The electronic circuitry within a computer that carries out the instructions of a computer program by performing the basic arithmetic, logical, control and input/output (I/O) operations specified by the instructions.

Computing device: A device that can be instructed to carry out an arbitrary set of arithmetic or logical operations automatically. The ability of computers to follow a sequence of operations, called a program, make computers very applicable to a wide range of tasks.

Configured package: One or more recommended complementary product items, services, and result that are grouped together in a bundle to streamline a decision making process and allow a user to expedite a purchase process. Also known as 'a package' or 'intelligent configured package' when provided as a result of a determine best result engine.

Consumer facing options: The features offered to a person or thing that consumes.

Consumer facing options input: The input provided by a consumer in response to the consumer facing options.

Contributor engine (also known as a Knowledge Engine): A software program and computer hardware capable of capturing and analyzing information of a predetermined type for presentation to a determine best package engine.

Criteria: One or more principles or standard by which the DBR can utilize to make an objective judgement or decision.

Criteria maintenance form: A user interface to allow an administrator to establish and maintain a scenario.

Customer: A person who purchases one or more of: goods, services, and results from another; buyer; patron. Also, referred to as a user or consumer.

Customer preferences engine (CPE): A computer hardware-software engine that captures customer preferences.

Customer's purchase history engine (CPH): A computer hardware-software engine that collects the previous purchases of product or services by a consumer.

Determine best results engine (DBR): A computer hardware-software engine that completes processes to determine an optimal matching result for a customer based on input from contributor engines.

Diagnostics: Characteristics of a particular product comprising one or more of: species, entity, condition, virus and illness.

Diagnostics engine (DPE): A computer hardware-software engine that processes data from one or more diagnostic devices including but not limited to programmable logic controllers, radio frequency devices, computing devices and various instrumentation devices. The diagnostics engine supports data in a structured or non-structured format.

E-Commerce: A transaction of buying or selling online any one or more of: goods, services, and results.

Ecommerce/cart solution: The software programs that enables the completion of the transaction of buying or selling online.

Engine: A computer processor responding to instructions of a computer program that collects and analyzes data.

Element: Any real or intangible item that produces a result of value to humans or computing devices.

Event: The outcome, issue, or result of anything.

Event characteristics: The related characteristics of an activity.

Event maintenance form: A user interface to allow an administrator to establish and maintain an event or activity.

Event sizes: The number of participants (human or thing) for an activity.

Event styles: The related styles of an activity.

Financial Services Engine (FSE): A computer hardware-software engine that processes financial data from one or more financial platforms (sources) to determine if it matches specified criteria. The financial data may include but is not limited to historical and current revenue, profit, loss, cost, and expense detail. It may also include future projections for revenue, profit, loss, cost, and expenses.

First user: The initial person who uses a computer or network service to interact.

Hierarchy: Any system of persons or things ranked one above another.

Inventory: A complete listing of merchandise or stock on hand.

Inventory availability engine (IAE): A hardware-software engine that collects available inventory counts for products or services across one or more sellers.

Knowledge data: The data resulting from analyzing captured information of a predetermined type by a knowledge engine.

Knowledge engine (also termed knowledge data engine): Computer hardware and associated software capable of capturing and analyzing information of a predetermined type to produce knowledge data.

Logic rules: A logic rule can be composed of a Boolean (true or false), if then else metaphor, or an expression that is to be performed on one or more objects.

Messaging: The sending and processing of email and similar electronic communications.

Messaging Processing Engine (MPE): A computer hardware-software engine that processes messages from one or more messaging platforms (sources) to determine if it qualifies for a specified set of criteria such as source, one or more destinations, date/time attributes, subject, content, key word matches and other meta fields. Sources are based on but not limited to protocols such as POP, SMTP, IMAP, MSNP, MTPROTO, MUMBLE, OSCAR, ICQ, and XMPP.

Online: Connected by computer to one or more other computers or networks, as through a commercial electronic information service or the Internet.

Online party planner: The processes of planning or scheduling an event or activity online.

Optimal package of goods: The best or most favorable set of products.

Package to event maintenance form: A user interface to allow an administrator to establish and maintain a relationship between the product packages and activity.

Package maintenance form: A user interface to allow an administrator to establish and maintain the related products in a set or bundle.

Planned event: A scheduled activity.

Planning service system: The process of making a plan or schedule for a product or service. The system includes legal, economic, political, social, and cultural aspects managed by interacting components.

Plurality of selections representing various types of events: Multiple available options identifying different characteristics of an event or activity. An example for events would be birthday, graduation, wedding, etc.

Presorted goods: Any one or more of products, services, and results sorted in advance.

Product items: A component of a goods or services produced by labor.

Product satisfaction engine (PSE): A hardware software engine that collects one or more of contentment, fulfillment, and gratification for products or services based on but not limited to customers rating, reviews and feedback.

Planning service system: A planning system covers the methods of planning.

Product: Goods or services produced by labor.

Product-element table: The details of one or more of a product, service, and result in an arrangement of data in rows and columns or more complex structure.

Processing a sale: The steps necessary to complete or abort a transaction.

Purchase: To acquire by the payment of money or its equivalent; buy.

Quality Assurance Engine (QAE): The quality assurance engine processes data from one or more quality devices including but not limited to programmable logic controllers, radio frequency devices, computing devices, robotic devices, and various instrumentation devices. The quality assurance engine supports data in a structured or non-structured format.

Rating: The classification according to grade or rank.

Recursion: Recursion is the process a procedure goes through when one of the steps of the procedure involves invoking the procedure itself.

Recursive: A procedure that goes through recursion.

Results: One or more preferred or optimal outcomes generated by the Determine Best Result knowledge engine.

Returning customer feature: Software programs instructing hardware that allows a customer to complete repeat purchases with the minimal information required to complete the transaction.

Review: A critique of a product or service.

Rules: An explicit set of fact criteria that must be met used by the DBR to determine its knowledge processing, organization of the truth table and truth pyramids, and processing path.

Sales History of All Consumers Engine (SHE): A hardware-software engine that collects the sales history of all consumers to which data is available.

Satisfaction: Contentment, fulfillment, gratification.

Scenario: An outline of the logical boundaries and elements needed for the DBR. The DBR can be processing one or more scenarios and/or sub-scenarios simultaneously or asynchronously.

Scenario maintenance form: A user interface to allow an administrator to establish and maintain a scenario.

Search Engine: A computer program that searches documents, especially on the World Wide Web, for a specified word or words and provides a list of documents in which they are found.

Search engine statistical results engine (SRE): A hardware-software engine that collects search engines results and metrics from search engines.

Selected events: The event or activity that the user chooses.

Social Media: Websites and other online means of communication that are used by large groups of people to share information and to develop social and professional contacts Social media trending engine (SME): A hardware-software engine that collects content from social media.

Storage portions of a computing device: The internal or external memory in a computing device.

Streaming Processing Engine (SPE)—The streaming processing engine processes video and audio streams. The streaming protocol utilized is but not limited to the SIP (Session Initiation Protocol). The streaming processing engine analyzes the meta data from the one or more streams coming from one or more streaming platforms to determine if it qualifies for a specified set of criteria. At the simplest form it analyzes the title, author, subject matter, content, participants, elements, and geographic location.

Three or more knowledge bases: Three or more of a knowledge base (KB) is a technology used to store complex structured and unstructured information used by a computer system.

Total cost: The quantity multiplied by price for all items. May include taxes and shipping.

Truth pyramid: The combination and grouping of related truth tables in a hierarchy to determine a resulting truth value of true or false.

Truth statements/Truth Tables: Truth tables involving n statements will have rows unless additional information about the truth values of some of these statements is known. A statement that is always true is called logically true or a tautology. A statement that is always false is called logically false or a contradiction.

Types of events: The category or sub-category of an activity.

Web service system: A web service is a computing process offered by an electronic device to another electronic device, communicating and interacting with each other.

In one form, a web service system is utilized to match a preferred package of medicines that is matched to an individual's diagnosis and ability to pay due to constraints of their financial situation or current insurance provider.

In one form, a web service system is utilized to match a preferred package of parts or sub-components to a specific manufacturing process requiring specific quality requirements and cost model.

In one form, a web service system is utilized to match a preferred package of financial assets to an entities investment portfolio and limited by the constraints of their financial situation and/or current economic conditions on a local, national, and global basis. This may include but is not limited to the appropriate allocation between stocks, commodities, bonds and cash and the re-distribution allocations within an investment category.

In one form, a web service system is utilized in preparation for a party or other event being planned requiring an assortment of goods.

In one form, a web service system is utilized in preparation for completing a task that requires an assortment of services.

In one form, a web service system is utilized in preparation for completing a task that requires a combination of two or more of results, products and services.

In one form, a web service system is utilized in preparation for completing a task that requires an assortment of preferred outcomes or results.

In one form, a web service system simplifies a purchasing process by streamlining and offering configured packages of assorted goods required in planning of an event. Stationary and mobile computing users experience reduced information overload and an easy purchasing experience using intuitive project planning and goods ordering systems.

In one form, a web service system is in the form of a determine best package (DBP) web service system which utilizes intelligence gathered by a plurality of knowledge data engines (contributor engines) to suggest smart configured packages of one or more of goods, services, and results to customers.

In one form, a determine best package (DBP) web service system comprises two or more contributing knowledge data engines that compile data to a determine best result data engine (DBR).

In one form, a configuration package includes party ware items such as table settings, napkins, decorations, and party favors needed by a customer for a hosting a party.

In one form, a configuration package may be a complete solution which includes all items required to complete a task based on original input by a customer.

In one form, a configured package offered by a web service system is based on original customer input which may include for example one or more of preferences, parameters, and suggestions.

In one form, a configuration package solution provided by a web service system will integrate with any ecommerce/cart solution such as but not limited to Amazon®, PayPal®, Ebay®, 7ware®, and others.

In one form, a web service system will utilize online catalogs of goods as a base to create an enhanced e-commerce solution.

In one form, a web service system will include an easy-to-use online party planner enabling users to easily select and purchase pre-assorted goods related to a planned event. A planned event may include any planned social activity involving two or more people. Examples of planned events include; family gatherings, dinner, birthdays, date night, first communion, vacation, etc.

In one form, benefits of a web service system include; saving user time through an easy to use system, ecologically friendly by reduction of extra or erroneous product that is not needed, increased cross sell of products by providing a complete package of ideal supplies and services for a task or event, re-occurring sales for embodiments including a returning customer feature, and a system enabled for mobile devices as well as desktop using web application framework such as ASP.Net and HTML 5 to produce dynamic web pages.

In one form, a web service system is web browser and computing device agnostic.

In one form, a web service system utilizes a header graphic, font, font size, and font color configured within a custom style sheet (.css). These attributes are linked to a unique URL with unique identifier so many sites can be supported having customer facing features having various looks and feels.

In one form, a web service system uses a "wizard" metaphor to make it easy to execute within an iframe.

In one form, a minimum size for an iframe will be height 650 pixels by width of 550 pixels.

In one form, a web service system comprises features displayed on screens of a computing device in communication with the web service system. Administrative facing features are features of a web service system displayed on a computing device accessible by an administrator for controlling operation of the system. Consumer (also known as customer or user) facing features are features of a web service system displayed on a computing device in communication with the web service system wherein the computing device is accessible to a consumer (i.e. a client system).

In one form, an administrative facing feature is in a package maintenance form. A package maintenance form provides administrators a page where they select products based on one or more of product ID, SKU, and product name from an existing product-element table to create groups of related products. These groups of related products are referred to as packages or configured packages.

In one form, a web service system comprises an administrative facing feature wherein an administrator is faced on a display screen with an editable form for adding new configured packages of goods to the system.

In one form, a web service system comprises an editable form for adding new configured packages of goods and further comprises an input on the form for a start date and an end date.

In one form, a web service system comprises an administrative facing feature wherein an administrator is faced on a display screen with an editable form for maintaining configured packages of goods wherein available goods may be removed or added to one or more configured package.

In one form, a web service system comprises an administrative facing feature further comprising an editable package maintenance form wherein said editable package maintenance form comprises a package search function to find existing configured packages within the system.

In one form, a web service system comprises an administrative facing feature comprising an add an event form. Using this form, an administrator may add selectable events to a web service system such as a child's birthday, a retirement, and anniversary. In one form, the add an event form includes a start date and end date.

In one form, a web service system comprises an administrative facing feature that is an event maintenance form for the creation of events. An example of an 'event' would be a child's birthday, an adult birthday, a retirement, a graduation, etc. Alternatively, an event may be a task such as refinishing a bench wherein goods within a configured package may be items such as a wire brush, sandpaper, paint, and paint brushes. As a further alternative, an event may be a task such as building a garage wherein a configured package may include both building supplies (goods) and a roofer (service).

In one form, administrative facing features are in a package to event maintenance form. A package to event maintenance form provides an administrator access to assign one or more available packages to a specific event type.

In one form, administrative facing features include access to edit a scenario to criteria maintenance form.

In one form, administrator inputs into administrative facing features and customer inputs into consumer facing features are saved to one or more storage portions of a computing device.

In one form, a web service system comprises consumer facing features. As defined herein, a consumer may be one or more of a consumer of goods and a business purchaser (also known as a customer or user).

In one form, consumer facing features are compatible with mobile electronic devices such as smart phones and tablets as well as with traditional web browsers used on a personal computer or laptop.

In one form, consumer facing features use a step-by-step "wizard" format resulting in a configuration package of items or services needed for an event they originally specified.

In one form, a consumer facing feature provides options for a user to choose between one or more event characteristics. Event characteristics may include one or more of the following: type of event, theme of event, event style, color preferences for an event, and other event details such as date of an event.

In one form, event characteristics are provided on a screen of a user's online access device in the form of a list of selectable menu choices. In one form the selection is in the form of an online accessible dropdown menu. In addition or alternatively, a field may be provided for the user to type in a few letters or words to search for a desired event characteristic.

In one form, one or more of a "GO" or "START" or similar initiation button is available to depress to begin a search or a search may be initiated by depressing a key such as "ENTER" on the keyboard.

In one form, a field may be provided to directly type in a known event characteristic such as 'BIRTHDAY' in a type of event field.

In one form, using information input by a user, picture icons of various event characteristics are presented by a web service system as an option for the user to search for event characteristic by picture.

In one form, radio buttons may be provided to enable a user to move through groups of featured images representing different event characteristics. A "CANCEL" button is also available to cancel a search.

In one form, an event characteristic is an event type selection. The event type selection provides the consumer a list of selectable events such as birthday, wedding, 1$^{st}$ communion, anniversary, etc.

In one form, an event characteristic is an event theme selection. An event theme provides a customer a list of selectable theme options for their event. Event themes extend from but are not limited to one or more of existing categories and sub-categories where only the category description is displayed to the user.

In one form an event characteristic is an event style and/or color selection. This selection provides a consumer a list of selectable styles and colors. In one form an event style and color selection extends from an existing table. In other forms a selection extends from a base of a SKU provided by a supplier. Each have a base and a suffix.

In one form an event characteristic is an event detail. An event detail provides the consumer a selection of options to define details of their event. Event details may include for example: number of attendees, number of tables, size of tables, shape of tables, child or adult event, and other relevant details related to the event.

In one form, following the selection of event characteristics by the consumer, the user is confronted with various options of packages of goods configured to fulfill event characteristics input by a customer. Displayed with each configuration package may be a total price of the package along with an option of recalculating price if a consumer chooses to adjust one or more event characteristics such as number of attendees.

In one form, event characteristics and pricing are savable and associated with a customer's email address or other login feature such as a user ID and password if a customer chooses to sign into the online system.

In one form, saved event characteristics and pricing are emailable to a third party such as a friend by inserting the third party's email address.

In one form, a system includes a buy feature which will proceed to insert chosen items in a configuration package into a new or existing online shopping cart. A consumer may then proceed to purchase chosen goods using known ecommerce methods.

In one form, a web service system includes instructions to a user for processing a sale and saving input by a user to a storage portion of the device.

In one form, a start over function button is clickable by the user to cause the system to clear previous inputs and return to the event type selection screen.

In one form, a cancel button is provided for exiting the online program.

In one form, a web service system will present a customer one or more configuration packages of goods compiled as a result of the initial event characteristics input by the user and one or more additional data sources.

In one form, a consumer facing feature in a web service system is in the form of a recommended package and results form displaying to a user configured packages of goods meeting parameters input the system by a customer.

In one form, a recommended package and results form will display the consumer's inputs.

In one form, a recommended package and results form displays clickable icons of featured images of recommended package items.

In one form, a recommended package and results form displays one or more of a clickable; buy button, a price guarantee button, a save button, and a cancel button.

In one form, in addition to a configuration package based solely on the consumer's event preferences, determine best package configuration packages may also be offered to a customer.

In one form, a determine best package (DBP) web service system processes data from three or more knowledge engines that stores one or more logic rules for one or more individual product items that make up a configuration package. An engine is a core service for storing, processing, and securing data. An engine may also be described as a computer processor responding to instructions of a computer program that collects and analyzes data. A DBR engine uses knowledge bases of contributing knowledge engines and logic rules within these knowledge engines to determine best possible matches for the resulting items within configuration packages. A DBR engine is based on inputs from any three or more of the contributing knowledge data engines (CPE, SME, SRE, SHE, IAE, PSE, ADR, CPH, SPE, MPE, DPE, FSE, QAE etc.). Each knowledge data engine is described in greater detail below. Each contributing knowledge data engine creates and shares truth tables for its specific functional area to a DBR engine.

In one form, one or more knowledge engines (CPE, SME, SRE, SHE, IAE, PSE, ADR, CPH, SPE, MPE, DPE, FSE, QAE) can be absent from a web service system.

In one form, one or more truth tables is logically cached into ram for best performance.

In one form, one or more truth tables is physically stored in cloud for processing.

In one form, a DBR processing approach can be used across many different retail sectors and industries including but not limited to manufacturing, healthcare, and financial.

In one form, a DBR engine performs calculations near real-time and returns to a user the best possible aggregated results. Re-calculation may be completed as needed based on updated preferences at run-time.

In one form, a DBR engine minimizes truth statements per matrix (table) to speed processing thereby providing near real-time processing. Using Morgan's Law the number of computations becomes exponential at 2 to the X power where X is the number of truth statements. Truth statements are reduced by use of a pyramid methodology wherein one or more optionally nested truth tables are used to calculate final results for each item of a package and an overall configured package. Truth pyramids which are made of three or more truth tables can be traversed recursively if necessary. Optimal performance is achieved by minimizing the number of logic rules (truth statements) per table and the number of tables per pyramid and number of pyramids overall. Additionally, performance may be enhanced further by nesting tables and utilizing a distributed parallel processing environment.

In one form, a determine best result engine (DBR) utilizes data collected from one or more data engines focused on; customer preferences (CPE), a customer's purchase history (CPH), sale's history of all consumer's (SHE), product satisfaction record (PSE), inventory availability (IAE), current trends on social media (SME), search engine statistical results (SRE), and various other administration defined rules (ADR).

In one form, a determine best results engine (DBR) utilizes data collected from one more data engines focused on: streaming processing (SPE), messaging processing (MPE), diagnostics (DPE), financial services (FSE), and quality assurance (QAE).

In one form, user interface tools establish scenario definitions, criteria, and rules for the benefit of the web service system administrator. In addition, the DBR platform can establish its own scenario definitions, criteria, and rules to determine the best possible outcome without the use of a user interface.

In one form, contributing data engine results from bots, crawlers, web services, and similar applications are mapped into truth tables such that a determine best package web application is dynamic. As data grows in any one engine, an engine relies on a greater scope of data to calculate from. This provides improved performance of matching configured packages to customer desires and over the course of time eliminating the need for hardcoded data engine rules.

In one form, one or more computer processors are dedicated to processing data from a single data engine.

In one form, a single computer processor is dedicated to processing data from two or more data engines.

In one form, a DBP web service system comprises computing components located at a single location.

In one form, one or more computer processors are used to execute computer instructions in a web service system.

In one form, a first user interacts with a web service system through a client system computing device and consumer facing features.

In one form, a DBP web service system comprises computing components located at a plurality of locations. These components of the system may be running in parallel on one or more processors at each location simultaneously on one or more servers.

In one form, processors in a DBP web service system may be one or more of virtual, clustered, and network load balanced.

In one form, processors in a DBP web service system may be centralized on a closed bus or distributed.

In one form, a DBR engine is used for each available contributing engine to grow in data intelligence by filtering out one or more of irrelevant, obsolete, and erroneous results for a specific knowledge area represented by each contributing knowledge engine.

In one form, a DBR engine comprises greater processing power than individual knowledge engines contributing data to a DBR engine.

In one form, individual knowledge engines are provided scaled processing power as data volume in the knowledge engine grows.

In one form, a DBP web service system is utilized for creation of configuration packages of products for a customer.

In one form, a DBP web service system is utilized for creation of configuration packages of services for a customer.

In one form, a DBP web service system is utilized for creation of configuration packages of determined outcomes.

In one form, a DBR engine grows in intelligence (smarter) over time as it considers larger amounts of data from contributing engines.

In one form, individual data engines contributing to a DBR engine may be added or removed as needed for a particular customer and product segment.

In one form, a DBR engine utilizes data from a customer preferences engine (CPE). A CPE processes captured customer preference criteria from a customer's instant visit and any optionally saved previous visits. This data is used to generate a portion of logic rules for a DBR knowledge base and processing component.

In one form, a DBR engine utilizes data from a social media trending engine (SME). A social media trending engine crawls and interfaces with one or more currently available social media sites to determine popular and unpopular items and topics. Popularity is determined based by defined thresholds on key attributes such as like, dislike, love, happy, sad, angry and other emoticons in the current active user population. For example, if five percent of an active user population is liking, posting, sharing or commenting on the results of a sporting event this would be deemed as popular (true) and a logic rule would be added for the DBR component. A counter example would be if the topic is determined to be not popular (false) based on negative keyword detection then a corresponding logic rule will be created for the DBR knowledge base and processing component.

In one form, a DBR engine utilizes data from a search results engine (SRE). A search results engine crawls and interfaces with one or more currently available search engines to determine search terms or phrases that are currently generating substantial interest. Substantial interest is defined as an increase in traffic based on defined thresholds over the normal traffic history. An increase in traffic for a given search term or phrase would be deemed as popular (true) and one or more logic rules is added to a DBR knowledge base and processing component.

In one form, SME and SRE have a lifespan assigned to each of the associated logic tables created. A lifespan of data for these engines may be any predetermined length of time including daily, weekly, or monthly. In one form, one or more automated tasks continuously collects information and updates related logic rules. Precedence is calculated in reverse order of monthly, weekly, and daily of the logic rules and table for these contributing engines.

In one form, a DBR engine utilizes data from a sales history engine (SHE). A sales history engine uses purchase history data to determine popularity for a given time period. The purchase history may extend from one or more of internal and external sources. A high count of successfully completed purchases on a particular item would be deemed as popular (true) and one or more logic rules will be added to the DBR knowledge base and processing component. A low count of successfully completed purchases on a particular item would be deemed as unpopular (false) and one or more logic rules will be added to the DBR knowledge base and processing component.

In one form, a DBR engine utilizes data from an inventory availability engine (IAE). An inventory availability engine uses inventory data to determine availability for a given time period. An inventory availability engine may be pulled from one or more of internal and external sources. A high count of available inventory on a particular item would be deemed as popular (true) and a logic rule would be added for the DBR component. A low count of available inventory or back order condition on a particular item would be deemed as not popular (false) and create one or more logic rules that will be added to the DBR knowledge base and processing component.

In one form, a DBR engine utilizes data from a product satisfaction engine (PSE). A product satisfaction engine crawls and interfaces with one or more currently available major ecommerce engines. It rates and ranks sites to determine specific products that are generating positive and negative customer experiences. A PSE then utilizes actual satisfaction rankings after being standardized to a common scale as well as the total number of experiences across one or more sources to calculate either a positive or negative experience and create one or more corresponding logic rules to be added to a DBR engine knowledge base and processing component.

In one form, a DBR engine utilizes data from an administration defined rules engine (ADR). An administration defined rules engine provides an administrator a tool to perform one or more of create, update, inactivate and delete logic rules in a DBR knowledge base and processing component. Additionally, an ADR provides an administrator operational capability to perform one or more of the following:
  a. Create one or more overriding logic rules.
  b. Create one or more weighted conditions on one or more specific logic rules.
  c. Create one or more weighted conditions on one or more contributing engines (i.e. CPE, CPH, SME, SRE, SHE, IAE, PSE, SPE, MPE, DPE, FSE, QAE).
Administrative defined rules can be implemented through an automated process such as one or more of a web service and a bot. Alternatively, administrative defined rules can be implemented manually by an administrator. In one form, administrative defined rules can be implemented using a combination of manual and automated processes.

In one form, a DBR engine utilizes data from a customer purchase history engine (CPH). A customer purchase history engine processes captured purchase history from a customer on an instant visit and any optionally saved previous visits to generate a portion of logic rules for a DBR engine knowledge base and processing component. A CPH engine provides data to a DBR engine to identify preferred customer brands, themes and interests.

In one form, a DBR engine utilizes a logic notification engine (LNE). A logic notification engine alerts merchant subscribers via, email, text or web interface when pertinent additions or changes in logic rules have occurred. This engine has an administrative facing interface to maintain merchant subscribers and their options.

In one form, one or more external online stores such as Ebay®, Amazon®, Zulily®, and others are integrated into a DBR system as suppliers of goods utilized in a configuration package. In one form these external online stores are integrated using one or more of web services, XML, and other interface methods.

In one form, one or more external suppliers of manufacturing goods, medical supplies, or financial services are integrated into a DBR system as suppliers of one or more of goods, services, and results in a configuration package.

In one form, generating by a computing device processor of an online planning service system one or more configured packages of goods comprises the step of said determine best results engine filtering out one or more of irrelevant truth statements, truth tables, and results that do not match one or more of identified product, product to event mapping, and rules defined by one or more of an administrator, a user, and the result of the determine best results web service.

In one form, generating by a computing device processor of a web service system one or more configured packages of determined outcomes comprises the step of said determine best results engine filtering out one or more of irrelevant truth statements, truth tables, and results that do not match one or more of scenarios, or criteria, and rules defined by one or more of an administrator, a user, and the result of the determine best results web service.

In one form, generating by a computing device processor of an online planning service system one or more configured packages of goods comprises the step of said determine best results engine filtering out one or more of obsolete truth statements, truth tables and results that are one or more of down trending and diminishing over a predetermined period of time.

In one form, generating by a computing device processor of an online planning service system one or more configured packages of goods comprises the step of said determine best results engine filtering out one or more of erroneous truth statements, truth tables, and results that have been one or more of discarded and flagged by at least one customer.

In one form, generating by a computing device processor of an online planning service system one or more configured packages of goods comprises the step of said determine best results engine filtering out one or more of truth statements and truth tables that said determine best result engine is unable to use.

In one form, generating by a computing device processor of an online planning service system one or more configured packages of goods comprises the step of said determine best result engine automatically adding one or more of positive and negative truth tables to a contributing knowledge engine in response to a returned product from a sale.

Computing devices interfacing with a web service system may include; one or more processor(s), one or more memory device(s), one or more interface(s), one or more local or remote mass storage device(s), one or more of Input/Output (I/O) device(s) such as a mouse and keyboard and voice recognition and video and touch device, and one or more display, all of which are coupled to a bus. Processor(s) include one or more processors and controllers that execute instructions stored in memory device(s) and mass storage device(s). Processor(s) may also include various types of computer-readable media, such as cache memory.

Memory device(s) within a web service system may include one or more various computer-readable media, such as volatile memory (e.g., random access memory (RAM)) and nonvolatile memory (e.g., read-only memory (ROM)). Memory device(s) may also include rewritable ROM, such as flash memory. A memory device may also be in the form of mass storage device(s) including various computer readable media, such as magnetic tapes, magnetic disks, optical disks, solid-state memory (e.g., flash memory), and so forth. Mass storage devices may be in the form of a hard disk drive to serve various computing devices. Various drives may also be included in mass storage device(s) to enable reading from and/or writing to the various computer readable media. Mass storage device(s) may include removable media and/or non-removable media.

Memory may be used for storing an operating system, application programs such as web browsers, other program modules, and program data. I/O device(s) include one or more of various devices that allow data and other information to be input to and retrieved from computing device(s). Example I/O device(s) include one or more of; cursor control devices, keyboards, keypads, microphones, monitors and other display devices, speakers, printers, network interface cards, modems, lenses, CCDs and other image capture devices, and the like.

Display devices include any type of device capable of displaying information to one or more users of a computing device in communication with a web service system. Examples of display devices include a monitor, display terminal, video projection device, and the like. A monitor and other types of display devices may also be connected to a system bus via an interface, such as a video interface. A graphics interface may also be connected to a system bus. One or more graphics processing units (GPUs) may communicate with a graphics interface. In this regard, GPUs generally include on-chip memory storage, such as register storage and GPUs communicate with a video memory. GPUs, however, are but one example of a coprocessor and thus a variety of co-processing devices may be included in a computer. In addition to a monitor, computers may also include other peripheral output devices such as speakers and printer, which may be connected through an output peripheral interface.

A bus allows processor(s), memory device(s), interface(s), mass storage device(s), and I/O device(s) to communicate with one another, as well as other devices and components coupled to the bus. Bus represents one or more of several types of bus structures including a memory bus and memory controller, a peripheral bus, a system bus, and a local bus using any variety of bus architectures. By way of example and not limitation, these may include PCI bus, IEEE 1394 bus, USB bus, ISA bus, MCA bus, EISA bus, and VESA local bus.

One of ordinary skill in the art can appreciate that a computer or other client device can be deployed as part of a computer network. In this regard, the present invention pertains to any computer system having any number of memory and storage units, and any number of applications and processes occurring across any number of storage units and volumes. The present invention may apply to an environment with server computers and client computers deployed in a network environment, having one or more of remote and local storage. The present invention may also apply to a standalone computing device, having programming language functionality, interpretation, and execution capabilities.

Interface(s) include various interfaces that allow any computing devices to interact with other systems, devices, and computing environments. Example interface(s) include any number of different network interfaces, such as interfaces to local area networks (LANs), wide area networks (WANs), wireless networks, and the Internet. Other interface(s) include user interface and peripheral device interface. An interface(s) may also include one or more user interface elements. An interface(s) may also include one or more peripheral interfaces such as interfaces for printers, pointing devices (mice, track pad, etc.), keyboards, and the like.

When used in a LAN networking environment, a computer is connected to the LAN through a network interface or adapter. When used in a WAN networking environment, the computer typically includes a modem or other means for establishing communications over the WAN, such as the Internet. A modem, which may be internal or external, may be connected to a system bus via a user input interface, or other appropriate mechanism. In a networked environment, program modules depicted relative to the computer, or portions thereof, may be stored in the remote memory storage device. By way of example and without limitation, remote application programs may reside on a memory device. It will be appreciated that network connections shown are exemplary and other means of establishing a communications link between the computers may be used.

Embodiments can also be implemented in cloud computing environments. In this description and the following claims, "cloud computing" is defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

For purposes of illustration, programs and other executable program components are shown herein as discrete blocks, although it is understood that such programs and components may reside at various times in different storage components of a computing device, and are executed by processor(s). Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions or code. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

These and other features and advantages of the present invention will become more readily appreciated when considered in connection with the following detailed description and appended drawings, wherein:

FIG. 13 is an illustration of one embodiment of just some of the various types of computer components that may be utilized within a determine best package web service system;

FIG. 14 is an illustration of one embodiment of a method of operation an administrator may use to input and maintain current relationship between events and goods and packages available;

FIG. 14B is an illustration of one embodiment of a method of operation an administrator may use to input and maintain various rules, scenarios, and criteria of determined results;

FIG. 15 illustrates one embodiment of an image displayed by a screen of a computing device an administrator may utilize to add a package of products available for a consumer to choose from in a consumer facing portion of a web service system;

FIG. 16 illustrates one embodiment of an image displayed by a screen of a computing device an administrator may utilize to link goods to packages available;

FIG. 17 illustrates one embodiment of an image displayed by a screen of a computing device an administrator may utilize to add one or more events to a list a consumer may choose from in a web service system;

FIG. 18 illustrates one embodiment of an image displayed by a screen of a computing device an administrator may utilize to link packages to events available in a determine best package web service system;

FIG. 19C is a spreadsheet illustrating examples of use of a web service system having a DBR engine for a variety of functions including but not limited to: online commerce, manufacturing, healthcare, and financial.

FIG. 23 illustrates one embodiment of an image displayed by a screen of a computing device providing one or more event detail selection choices to enable a customer to input event related details such as quantity in a web service system;

FIG. 24 illustrates one embodiment of an image displayed by a screen of a consumer's computing device wherein a web service system provides one or more recommended packages for purchase.

DETAILED DESCRIPTION OF SELECT EMBODIMENTS OF THE INVENTION

It is understood that components of the present invention as generally described and illustrated in the Figures disclosed herein could be designed and arranged in a variety of different configurations. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The present invention may be embodied as an apparatus, method, or computer program product and thus may take the form of a hardware embodiment, a software embodiment, or an embodiment combining software and hardware aspects referred to as a system.

Figure 1:
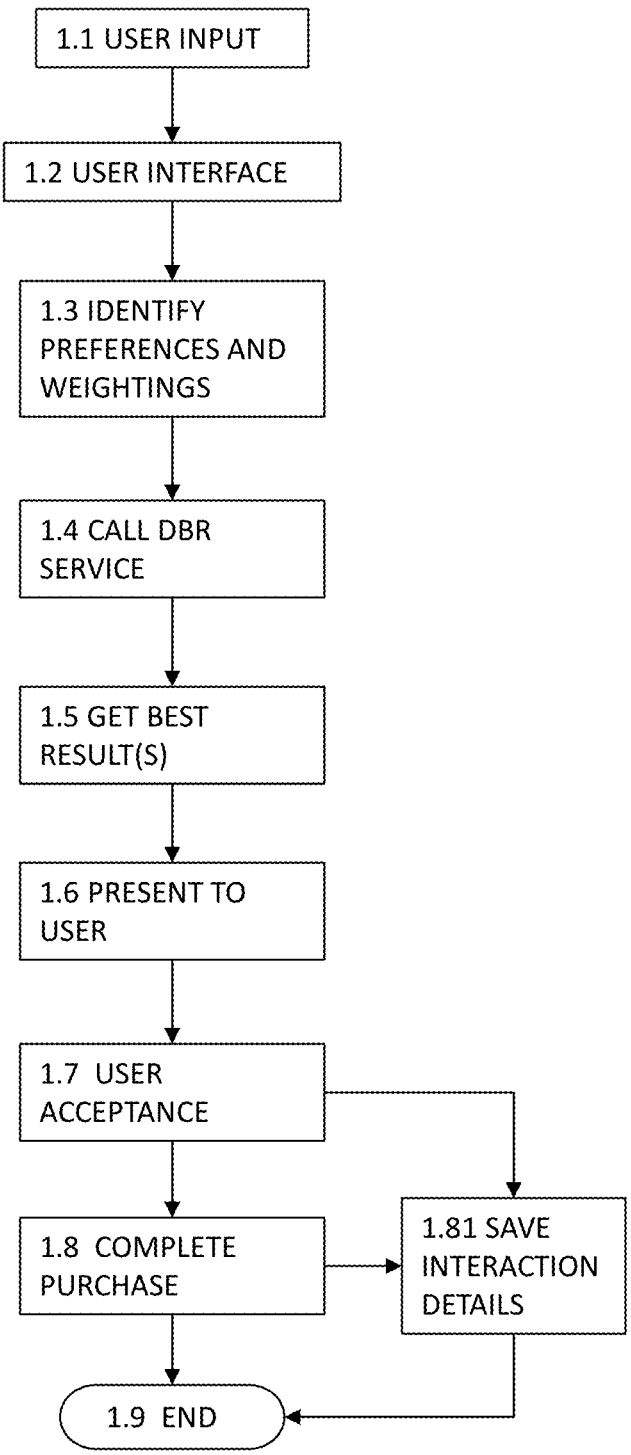
FIG. 1 is an illustration summarizing one embodiment of a method of operation of a web service system.

FIG. 1 is an illustration summarizing one embodiment of a method of operation of a web service system. At step 1.1, a user (customer) compiles preferences for a desired package of one or more of: goods, and services, and results. At step 1.2, the user interfaces with the web service system through a computing device communicating with the web service system to input the parameters from step 1.1 into the web service system. At step 1.3 the web service system identifies and processes on a computer processor the preferences of the customer and presents on a display 1.6 of a customer's computing device configured packages of goods fulfilling the defined preferences of the customer. In some embodiments, after identifying customer preferences 1.3, a web service system utilizes a determine best result engine 1.4 which utilizes information from a plurality of contributing knowledge data engines to present intelligent configured package recommendations to a user of one or more of: goods, services, and results. At this point, the customer reviews configured packages recommended by the web service system and can choose to accept one of the packages 1.7. For goods and services, the customer then completes the purchase using an online commerce system 1.8 and items are shipped to the customer. Purchase details may be saved into the web service system at 1.81. For a configured package of results, completing a purchase 1.8 may not apply although the interaction details are still saved 1.81. The process ends at 1.9.

Figure 1B:
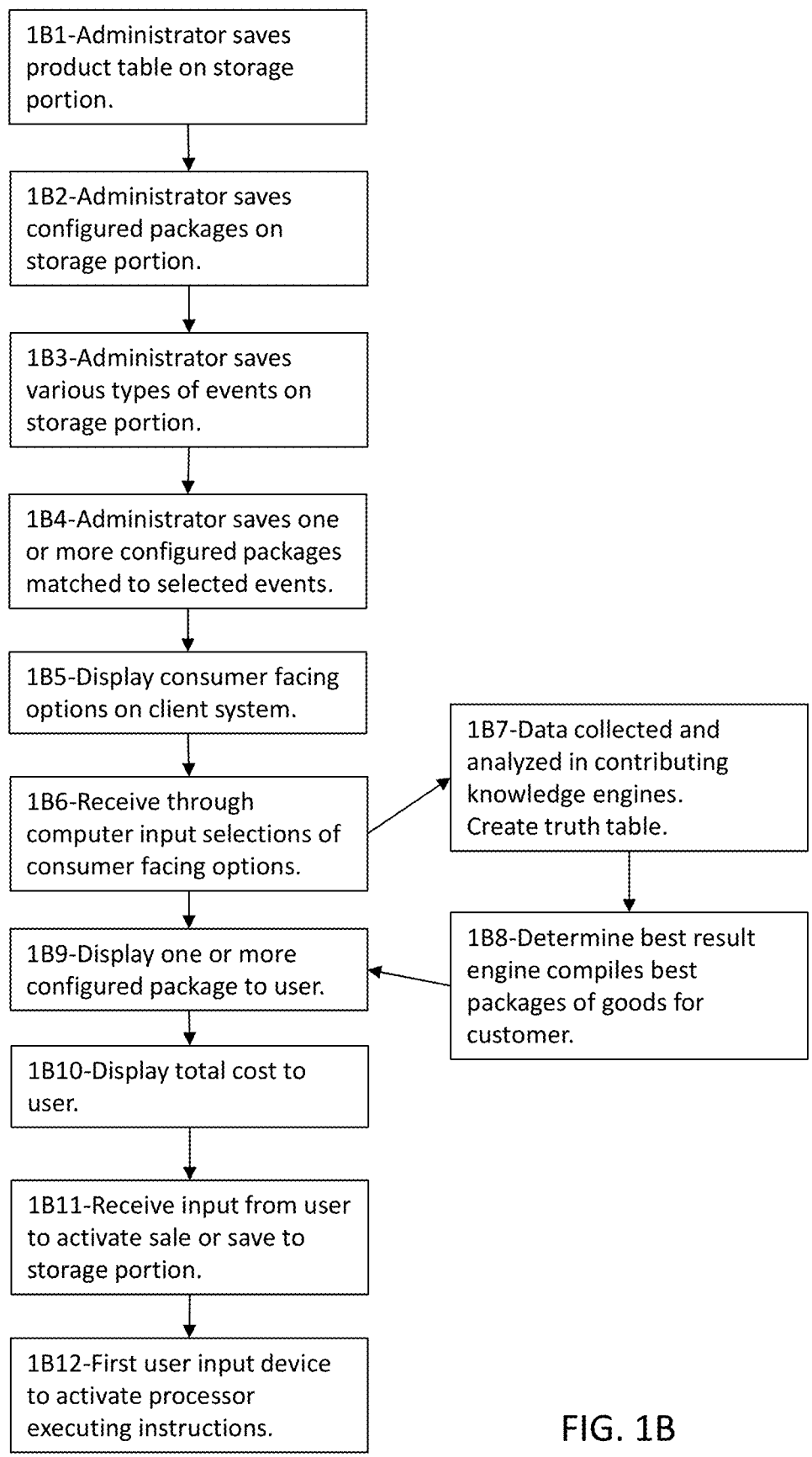
FIG. 1B is an illustration summarizing one embodiment of a method of operation of a web service system.

FIG. 1B is an illustration summarizing one embodiment of a method of operation performed by one or more computing devices of an online planning service system enabling users to easily select and purchase from a collection of one or more of pre-selected goods and presorted goods for a planned event. The illustrated method comprises the steps of saving on one or more storage portions of a computing device a product-element table referencing products for sale 1B1. Then saving on one or more storage portions of a computing device of said online planning service system one or more configured packages based on products available from said product-element table 1B2. Saving on one or more storage portions of a computing device of said online planning service system a plurality of selections representing various types of events from which a user may choose 1B3. Saving on one or more storage portions of a computing device of said online planning service system one or more configured packages matched to selected events 1B4. Displaying consumer facing options on a client system of a first user 1B5. In response to display of the consumer facing options to a first user, receiving from the first user through a computer input device, selections of consumer facing options 1B6. The system may proceed to display one or more configured packages to the first user at 1B9, or alternatively first compile data from three or more knowledge bases of a determine best results engine that stores one or more logic rules for the one or more individual product items that make up a configuration package 1B7. Then generating by a computing device processor of the online planning service system one or more recommended configured packages of goods corresponding to consumer facing option inputs received by said first user and data compiled from said determine best results engine 1B8. Then displaying on a client system of a first user, said one or more configured packages of goods 1B9, then displaying on a client system of a first user, a total cost of each configured package of goods 1B 10. In response to display of one or more configured package of goods, receiving from the first user instructions for one or more of: processing a sale and saving information input by the first user 1B11, then activating a computer processor of said online planning service system to execute said instructions from the first user 1B12.

Figure 1C:
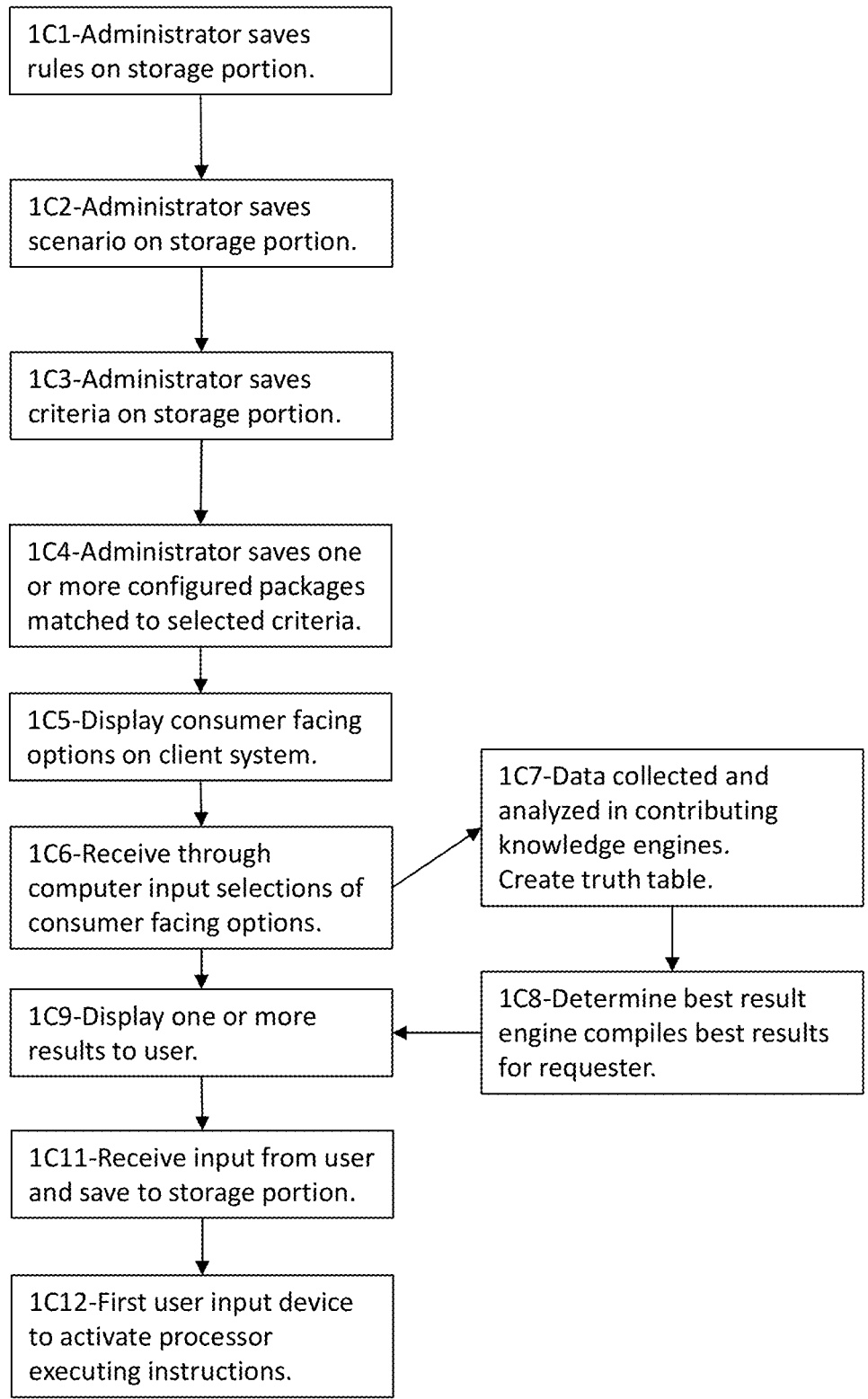
FIG. 1C is an illustration summarizing one embodiment of a method of operation of a web service system.

FIG. 1C is an illustration summarizing one embodiment of a method of operation performed by one or more computing devices of a web service system enabling users to easily select from a collection of one or more of pre-selected and presorted results for a defined scenario having specified criteria. The illustrated method comprises the steps of saving rules in a rules table on one or more storage portions of a computing device 1C1. Then saving on one or more storage portions of a computing device of said web service system one or more scenarios based on results available from said rules table 1C2. Saving on one or more storage portions of a computing device of said web service system a plurality of selections representing various types of criteria from which a user may choose 1C3. Saving on one or more storage portions of a computing device of said web service system one or more configured packages matched to selected criteria 1C4. Displaying consumer facing options on a client system of a first user 105. In response to display of the consumer facing options to a first user, receiving from the first user through a computer input device, selections of consumer facing options 106. The system may proceed to display one or more configured packages of results to the first user at 1C9, or alternatively first compile data from three or more knowledge bases of a determine best results engine that stores one or more logic rules for the one or more individual result items that make up a configuration package 1C7. Then generating by a computing device processor of the web service system one or more recommended configured packages of results corresponding to consumer facing option inputs received by said first user and data compiled from said determine best results engine 1C8. Then displaying on a client system of a first user, said one or more configured packages of goods 1C9. In response to display of one or more configured package of results, receiving from the first user instructions to save information input by the first user 1C11, then activating a computer processor of the web service system to execute the instructions from the first user 1C12.

Figure 2:
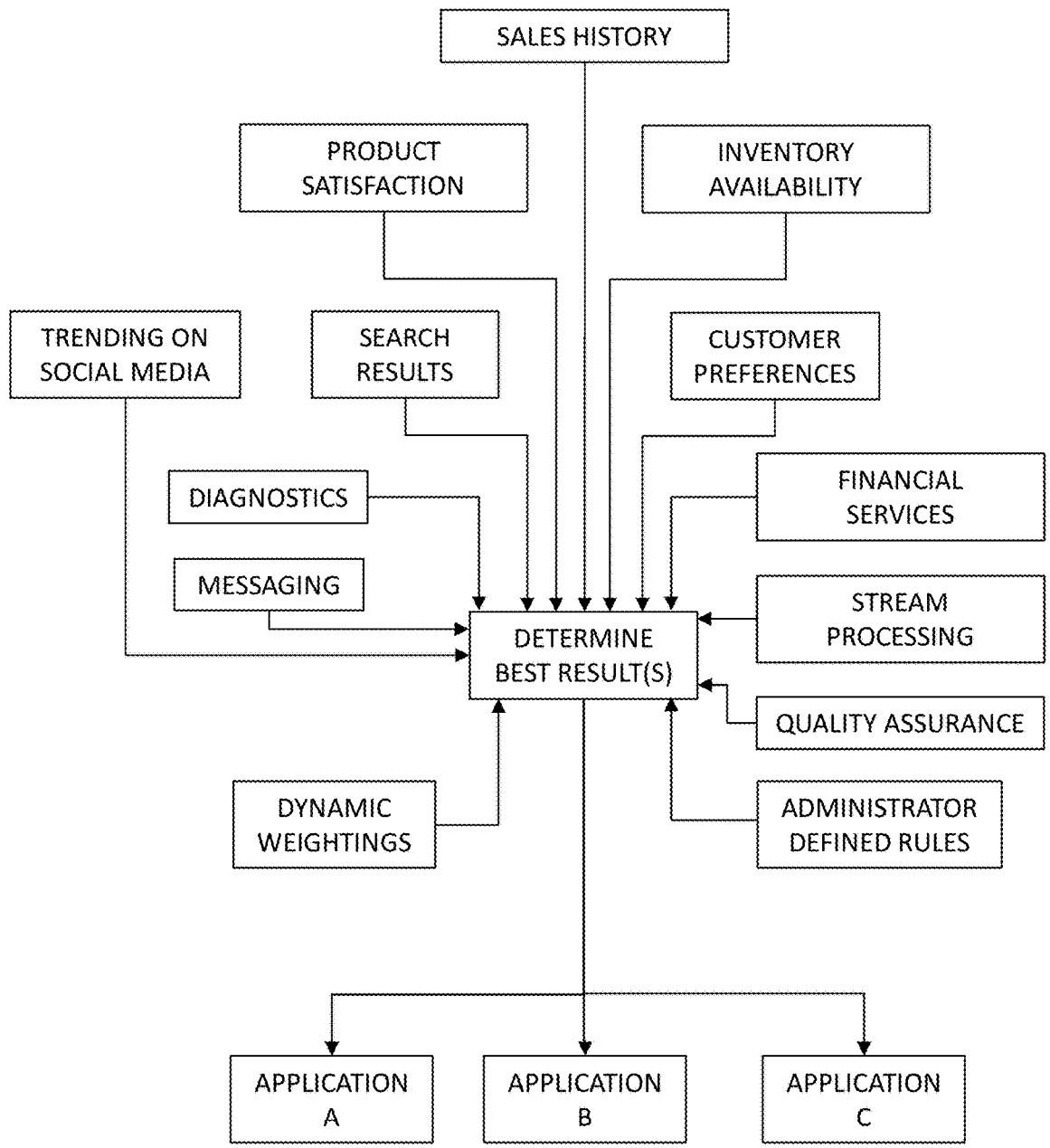
FIG. 2 is an illustration of one embodiment of a determine best result (DBR) engine collecting data from a plurality of contributing knowledge engines and outputting information to one or more applications.

FIG. 2 is an illustration of one example of an operational relationship between contributing knowledge engines and a determine best result data engine. In this embodiment, a DBR engine is in the form of a high speed server optimized for network performance and computational proficiency and efficiency. The server configuration is operating system independent and may be scaled by use of one or more of a network load balanced, clustered, and by sub-functional areas. In this embodiment, the DBR server configuration is a combination of server side components, internal data sources, external data sources, optional third party data sources and an administration rules creation engine to determine one or more "best" recommended configured packages of goods, services, and results for a customer. As illustrated, data engine sources may include but are not limited to customer's preferences, sales history, product satisfaction record, inventory availability, trends on social media for determining popularity (i.e. current movies, sports, entertainment, politics, etc.), search engine statistical results, customer purchase history, dynamic weighting of the various data, and an administration rules engine. In addition, data engine sources can include one or more of streaming processing, messaging processing, diagnostics, financial services, and quality assurance.

Figures 3A, 3B:
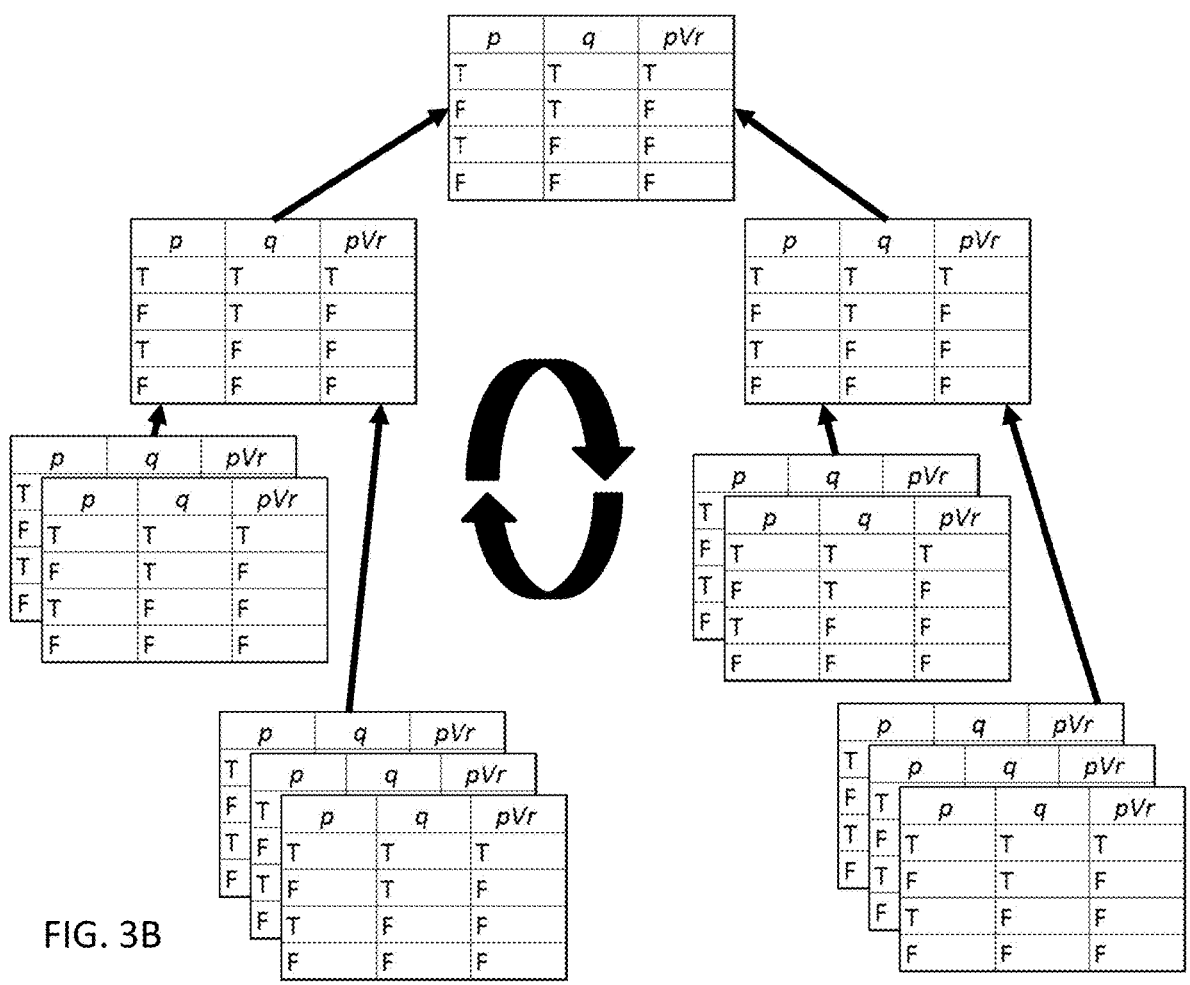
FIG. 3A is an illustration of one embodiment of nested truth tables collected into a determine best result engine (DBR)
FIG. 3B is an illustration of one embodiment of a flow of a determine best package results engine utilizing nested truth tables from multiple contributing data engines.

FIG. 3A is an illustration of one embodiment of nested truth tables collected for use in a determine best result engine (DBR) whereas FIG. 3B is an illustration of one embodiment of a flow of a determine best package results engine utilizing multiple nested truth tables within a hierarchy from a variety of contributing data engines.

Figure 4:
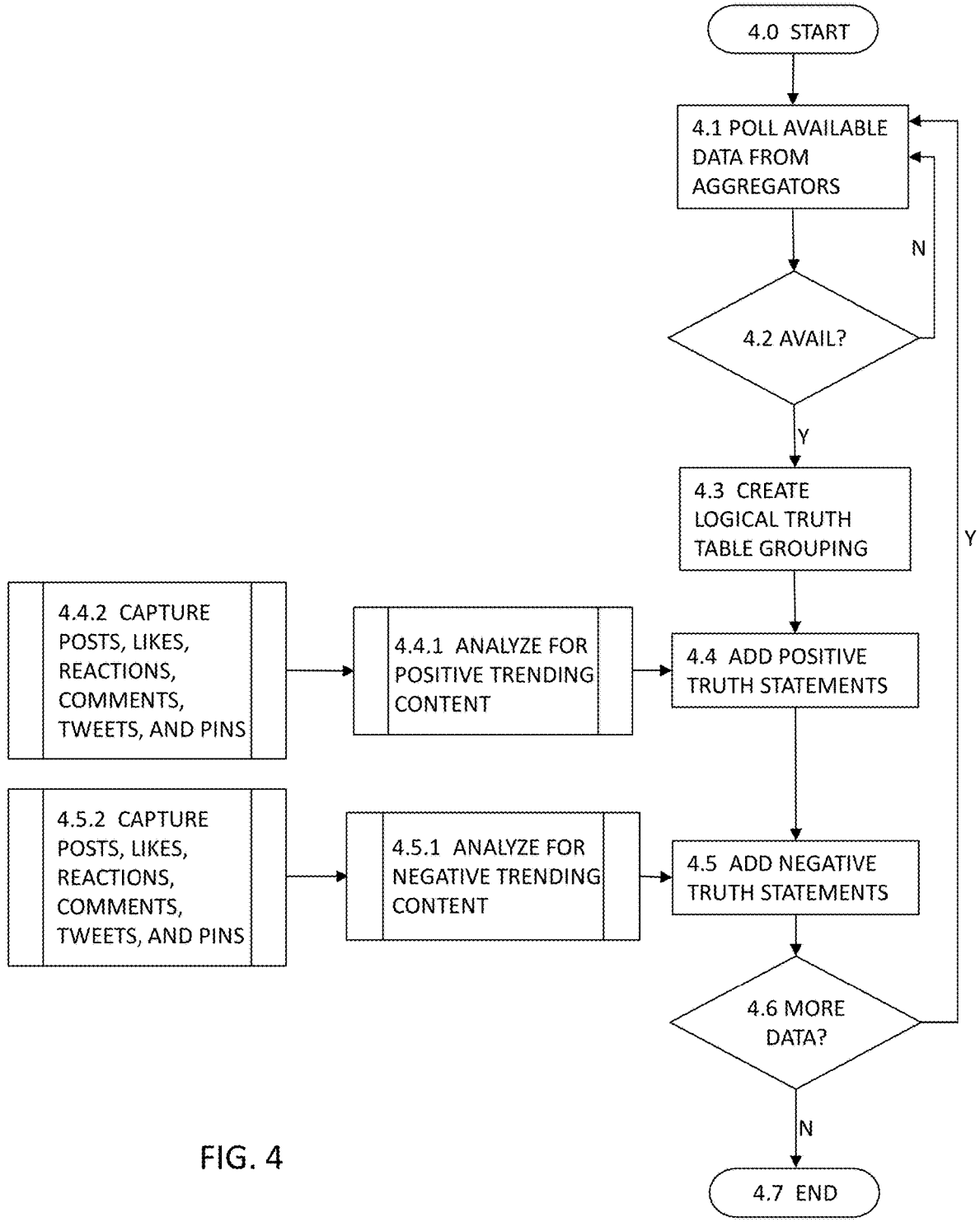
FIG. 4 is an illustration of one embodiment of a method of operation of a social media trending engine (SME)

FIG. 4 is a flowchart illustrating one embodiment of a method of operation of a social media trending engine (SME) starting at step 4.0. At 4.1 the SME polls available knowledge content from aggregators to determine topics that are one or more of popular and unpopular. Aggregators in the form of one or more of crawlers, bots, and web services will process from their available target source(s) and generate results. Target sources may include but are not limited to Facebook®, Google+®, Tumblr®, and Twitter®.

Data availability is determined at step 4.2. Available data is processed. If SME related data is unavailable, the process loops back to polling at step 4.1 immediately, at a preconfigured time, or at a designated action interval for repeat of step 4.1 until data is captured. Once polled SME data is available and captured, a check for results that already exist will be performed. If results do not exist, a logical grouping of truth statements is created at step 4.3 in one or more of memory and other computer storage mediums in the form of a truth table having a unique identifier. Truth table responses will be determined based by defined thresholds on key attributes in the current active user population. DBR engine processing performance speed will be enhanced if the SME truth statements are cached in memory.

Data is also captured when available from one or more of positive content 4.4.2 and negative content 4.5.2 related to a particular topic. Positive and negative reactions (i.e. posts, reactions, comments, views, likes, tweets, pins, polls, etc.) may be based on but not limited to keyword match rules, pattern recognition, and content analysis of post and get urls, etc. Captured positive trending content is then analyzed 4.4.1 based on but not limited to keyword match rules, pattern recognition, content analysis of post and get urls and compiled into one or more truth statements within a truth table extending from 4.3 for a specific identifier at 4.4. Captured negative trending content is analyzed 4.5.1 based on but not limited to keyword match rules, pattern recognition, content analysis of post and get urls, and compiled into one or more truth statements within a truth table extending from 4.3 for a specific identifier at 4.5.

At 4.6 a SME routine may end at 4.7 or may return to polling for available data from aggregators 4.1 if so desired. Data within a Social Media Trending Engine will have a limited useful life span assigned to each logic table created including daily, weekly, and monthly. One or more automated tasks will continuously be collecting the information and add/updating related logic rules. Precedence will be determined in reverse order of monthly, weekly, and daily of the logic rules and table for this SME engine due to changing social media trends over time.

Figure 4B:
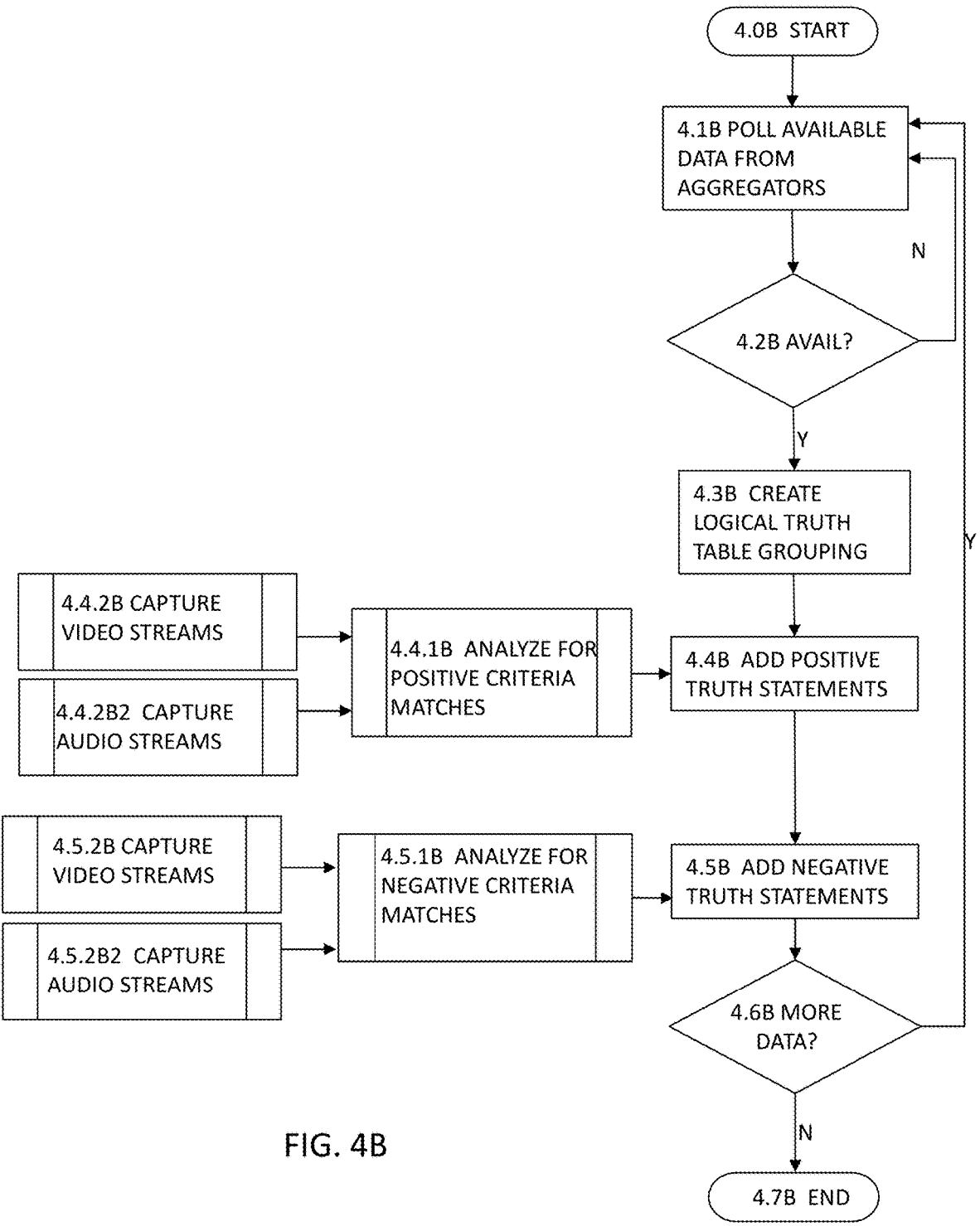
FIG. 4B is an illustration of one embodiment of a method of operation of a streaming processing engine (SPE)

FIG. 4B is a flowchart illustrating one embodiment of a method of operation of a streaming processing engine (SPE) starting at step 4.0B. At 4.1B the SPE polls available video streams and audio streams from aggregators to analyze the meta data from the one or more streams coming from one or more streaming platforms to determine if it qualifies for a specified set of criteria. At the simplest form it analyzes the title, author, subject matter, content, participants, elements, and geographic location. Aggregators in the form of one or more of crawlers, bots, and web services will process from their available target source(s) and generate results. Target sources may include but are not limited to Facebook®, Google®, YouTube®, Tumblr®, and Twitter®.

Data availability is determined at step 4.2B. Available data is processed. If SPE related data is unavailable, the process loops back to polling at step 4.1B immediately, at a preconfigured time, or at a designated action interval for repeat of step 4.1B until data is captured. Once polled SPE data is available and captured, a check for results that already exist will be performed. If results do not exist, a logical grouping of truth statements is created at step 4.3B in one or more of memory and other computer storage mediums in the form of a truth table having a unique identifier. Truth table responses will be determined based by defined thresholds on key attributes in the current active user population. DBR engine processing performance speed will be enhanced if the SPE truth statements are cached in memory.

Data is also captured when available from video streams 4.4.2B and 4.5.2B, and audio streams 4.4.2B2 and 4.5.2B2. The video streams 4.4.2B and audio streams 4.4.2B2 are analyzed for positive criteria matches 4.4.1B and compiled into one or more truth statements within a truth table extending from 4.3B for a specific identifier at 4.4B. The video streams 4.5.2B and audio streams 4.5.2B2 are analyzed for negative criteria matches 4.5.1B and compiled into one or more truth statements within a truth table extending from 4.3B for a specific identifier at 4.5B.

At 4.6B a SPE routine may end at 4.7B or may return to polling for available data from aggregators 4.1B if so desired. Data within a stream processing engine will have a limited useful life span assigned to each logic table created including daily, weekly, and monthly. One or more automated tasks will continuously be collecting the information and add/updating related logic rules. Precedence will be determined in reverse order of monthly, weekly, and daily of the logic rules and table for this SPE engine due to changing social media trends over time.

Figure 5:
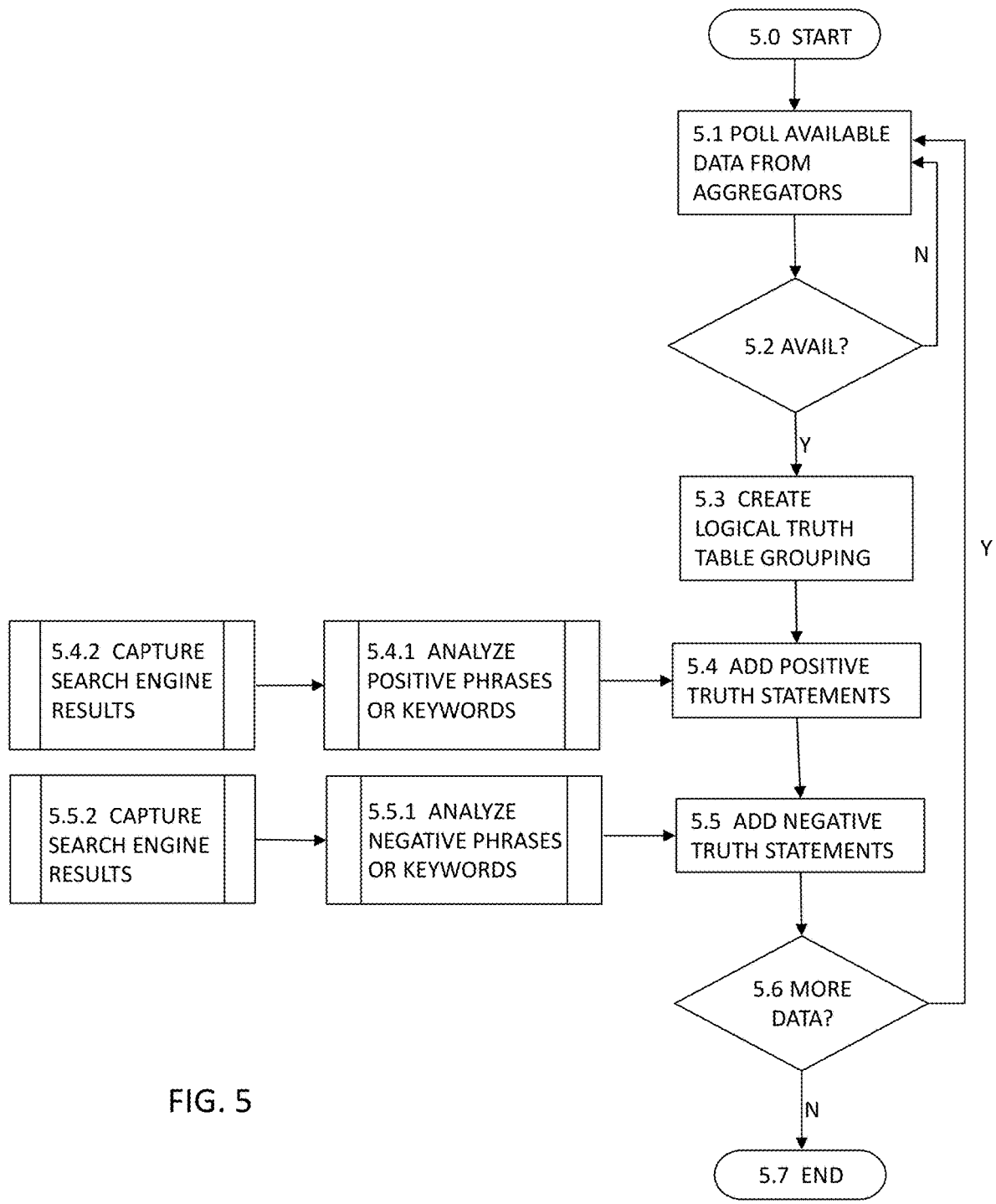
FIG. 5 is an illustration of one embodiment of a method of operation of a search results engine (SRE)

A search results engine (SRE) performs one or more of crawls and interfaces with currently available internet search engines to determine search terms and phrases that are currently generating substantial interest. FIG. 5 is a flowchart illustrating one embodiment of a method of operation of a search results engine starting at step 5.0. At 5.1 a SRE polls available knowledge content from aggregators (i.e. crawlers, bots, web services) and processes from their available target source then generates results. Target sources may be but are not limited to Google®, MSN®, Yahoo®, and the like and may be one or more of organic and paid placement.

Data availability is determined at step 5.2. If SRE related data is unavailable, the process loops back to polling at step 5.1 immediately, at a preconfigured time, or at a designated action interval for repeat of step 5.1 until data is captured. Once polled SRE data is available and captured, a check for results that already exist will be performed. If results do not exist, a logical grouping of truth statements is created at step 5.3 in one or more of memory and other computer storage mediums in the form of a truth table having a unique identifier. Truth table responses will be determined based by defined thresholds on key attributes in the current active user population. DBR engine processing performance speed will be enhanced if the SRE truth statements are cached in memory.

Data is also captured when available from one or more of; positive search engine results 5.4.2 and negative search engine results 5.5.2. Captured positive and negative search engine results comprise positive and negative trending metrics (i.e. likes, reactions, posts, comments and views) from one or more search engines. Captured positive and negative search engine results are then analyzed at 5.4.1 (positive) and at 5.5.1 (negative) based on but not limited to keyword match rules, pattern recognition, content analysis of post and get urls and compiled into one or more truth statements within a truth table extending from 5.3 for a specific identifier at 5.4 (positive) and 5.5 (negative). The truth statements are based on but not limited to the related positive or negative connotation of key phrases or words. Popularity can be determined by a variety of metrics.

As illustrated at 5.6, a SRE routine may end at 5.7 or may return to polling for available data from aggregators 5.1 if so desired. Data within a search results engine has a limited useful life span assigned to each logic table created including daily, weekly, and monthly. One or more automated tasks will continuously be collecting the information and add and updating the related logic rules. Precedence will be determined in reverse order of monthly, weekly, and daily of the logic rules and table for this SRE due to changing trends over time.

Figure 5B:
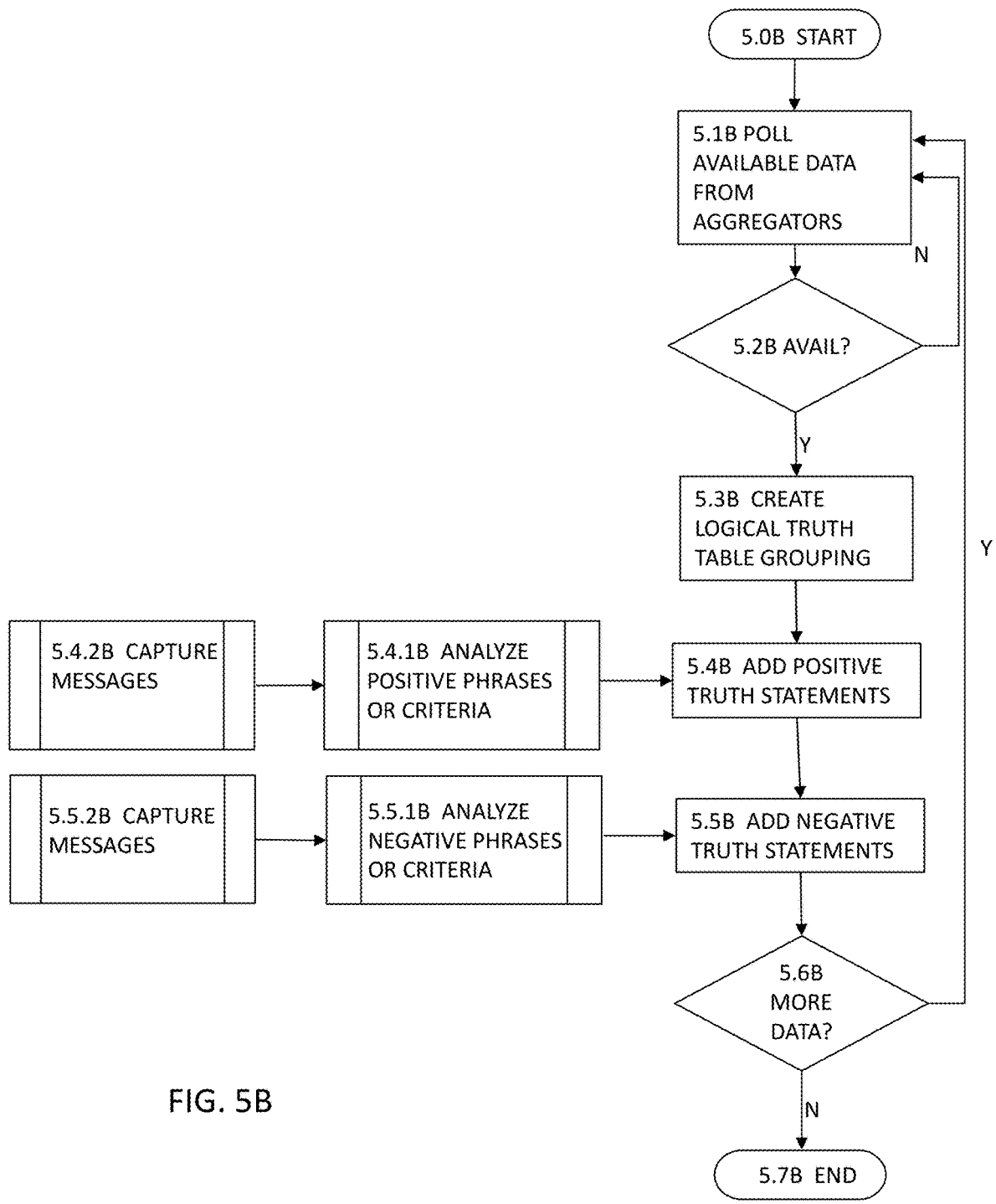
FIG. 5B is an illustration of one embodiment of a method of operation of a messaging processing engine (MPE)

FIG. 5B is a flowchart illustrating one embodiment of a method of operation of a messaging processing engine (MPE) starting at step 5.0B. At 5.1B the MPE polls available messages from one or more messaging platforms (sources) to determine if it qualifies for a specified set of criteria such as source, one or more destinations, date/time attributes, subject, content, key word matches and other meta fields. Sources are based on but not limited to protocols such as POP, SMTP, IMAP, MSNP, MTPROTO, MUMBLE, OSCAR, ICQ, and XMPP. Aggregators in the form of one or more of crawlers, bots, and web services will process from their available target source(s) and generate results. Target sources may include but are not limited to Facebook®, Google®, Tumblr®, Snapchat® and Twitter®.

Data availability is determined at step 5.2B. Available data is processed. If MPE related data is unavailable, the process loops back to polling at step 5.1B immediately, at a preconfigured time, or at a designated action interval for repeat of step 5.1B until data is captured. Once polled MPE data is available and captured, a check for results that already exist will be performed. If results do not exist, a logical grouping of truth statements is created at step 5.3B in one or more of memory and other computer storage mediums in the form of a truth table having a unique identifier. Truth table responses will be determined based by defined thresholds on key attributes in the current active user population. DBR engine processing performance speed will be enhanced if the MPE truth statements are cached in memory.

Data is also captured when available from messages 5.4.2B and 5.5.2B. The messages are analyzed for positive criteria matches 5.4.1B and compiled into one or more truth statements within a truth table extending from 4.3B for a specific identifier at 5.4B. The messages 5.5.2B are analyzed for negative criteria matches 5.5.1B and compiled into one or more truth statements within a truth table extending from 5.3B for a specific identifier at 5.5B.

At 5.6B a SPE routine may end at 5.7B or may return to polling for available data from aggregators 5.1B if so desired. Data within a messaging processing engine will have a limited useful life span assigned to each logic table created including daily, weekly, and monthly. One or more automated tasks will continuously be collecting the information and add/updating related logic rules. Precedence will be determined in reverse order of monthly, weekly, and daily of the logic rules and table for this MPE engine due to changing trends over time.

Figure 6:
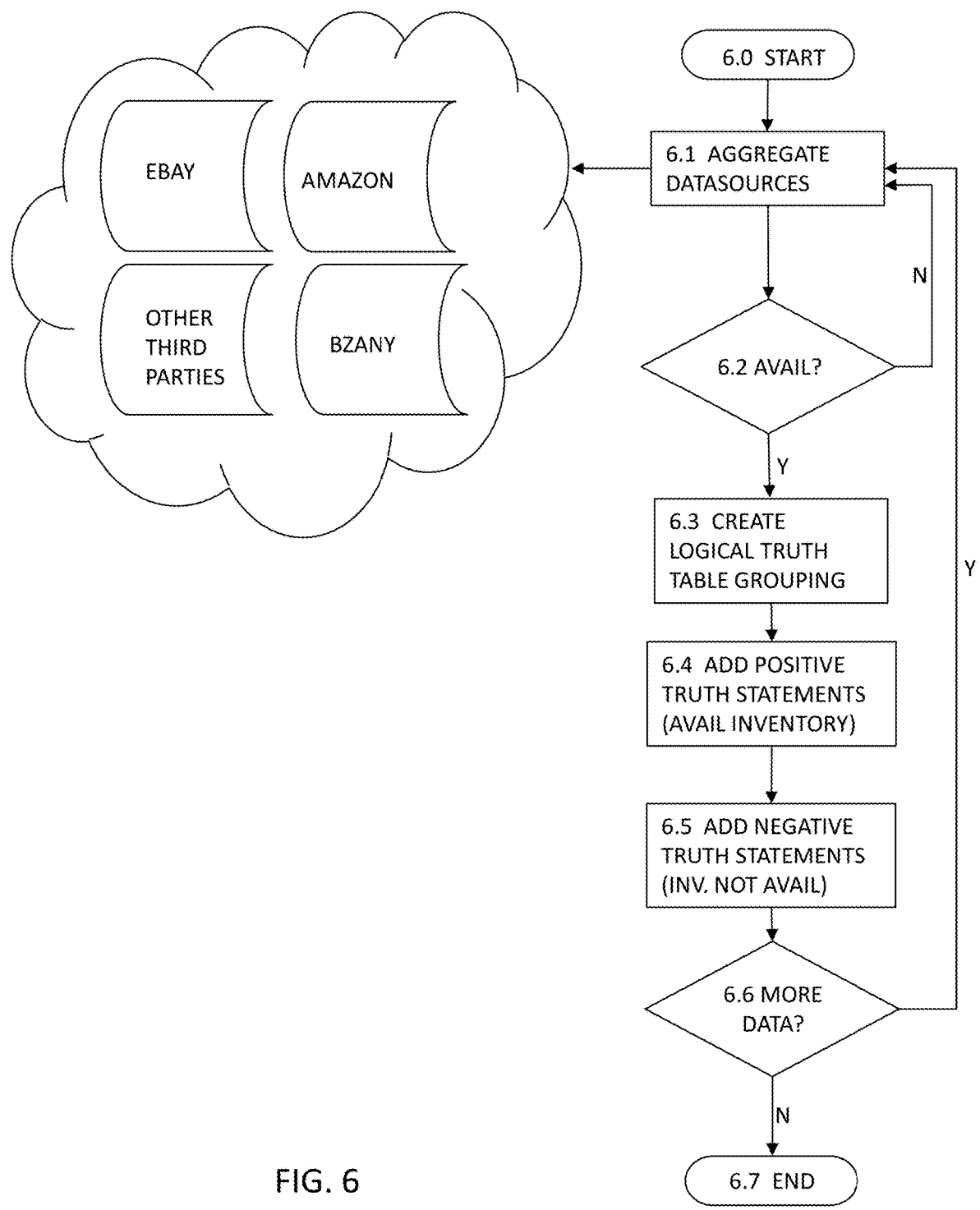
FIG. 6 is an illustration of one embodiment of a method of operation of an inventory availability engine (IAE)

FIG. 6 is a flowchart illustrating one embodiment of a method of operation of an inventory availability engine (IAE) starting at step 6.0. An inventory availability engine uses inventory data to determine availability of goods in inventory that may be used to create a configured package during a given time period. Data for an inventory availability engine is polled from one or more internal and external aggregate data sources (crawlers, bots, web service). The IAE then generates results when the data is available. FIG. 6 is an illustrative example of an aggregation of data regarding inventory levels for specified goods at Ebay®, Amazon®, Bzany®, and other third parties such as Walmart® and Zulily®. If inventory data is available, the information is processed. When inventory data is unavailable, the IAE routine loops back to step 6.1 where an IAE will continue to poll available knowledge content from aggregators immediately, at a configured time, or at a predetermined action interval. When inventory data is available, aggregated data is used to create logical truth table groupings at step 6.3. If inventory data does not already exist, a logical grouping of truth statements with a unique identifier is created in one or more of memory, disk, and a storage portion of an associated computing device. Caching the information in memory will provide optimal performance for DBR processing.

A high count of available inventory on a particular item would be deemed as positive (true) and a logic rule would be added for a DBR component at step 6.4. A low count of available inventory or back order condition on a particular good would be deemed as negative (false) and creation of one or more logic rules is added to a DBR knowledge base and processing component at step 6.5. Inventory goods in preferred embodiments are identified by UPC or GTIN. At this point, an IAE may loop back to poll available knowledge content from aggregators as described in step 6.1. If additional inventory data is unnecessary, IAE routines may end at 6.7.

Figure 6B:
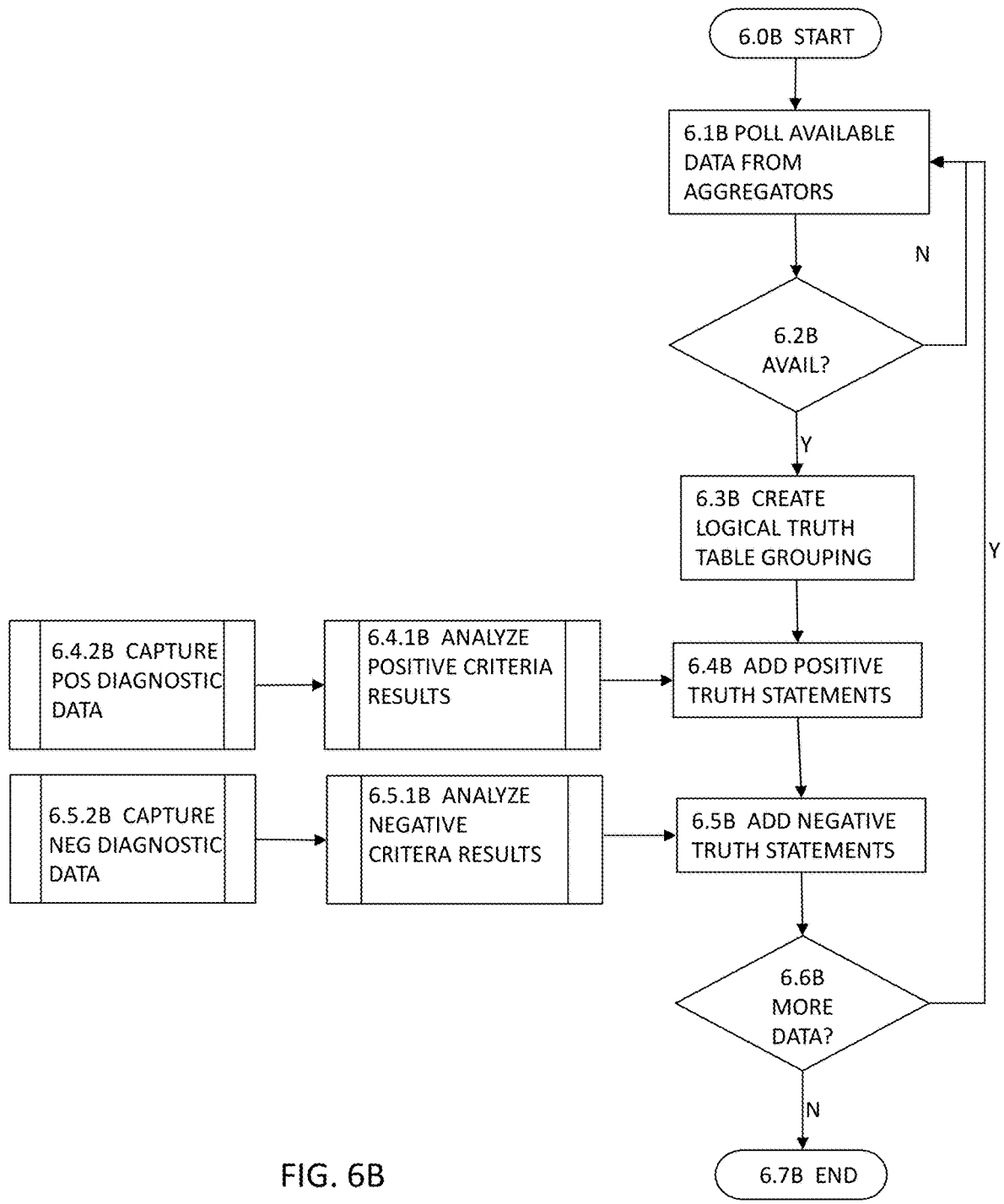
FIG. 6B is an illustration of one embodiment of a method of operation of a diagnostics engine (DPE)

FIG. 6B is a flowchart illustrating one embodiment of a method of operation of a diagnostics processing engine (DPE) starting at step 6.0B. At 6.1B the DPE polls available data from one or more diagnostic devices including but not limited to programmable logic controllers, computer numerical controls, sensors, robotic systems radio frequency devices, computing devices and various instrumentation devices. The diagnostics engine supports data in a structured or non-structured format. Aggregators in the form of one or more of crawlers, bots, and web services will process from their available target source(s) and generate results. Target sources may include but are not limited to LITMUS EDGE PLATFORM, ROCKWARE, SCADA SYSTEMS, and others.

Data availability is determined at step 6.2B. Available data is processed. If DPE related data is unavailable, the process loops back to polling at step 6.1B immediately, at a preconfigured time, or at a designated action interval for repeat of step 6.1B until data is captured. Once polled MPE data is available and captured, a check for results that already exist will be performed. If results do not exist, a logical grouping of truth statements is created at step 6.3B in one or more of memory and other computer storage mediums in the form of a truth table having a unique identifier. Truth table responses will be determined based by defined thresholds on key attributes in the current active user population. DBR engine processing performance speed will be enhanced if the DPE truth statements are cached in memory.

Data is also captured when available from messages at 6.4.2B and 6.5.2B. The messages are analyzed for positive criteria matches 6.4.1B and compiled into one or more truth statements within a truth table extending from 6.3B for a specific identifier at 6.4B. The messages 6.5.2B are analyzed for negative criteria matches 6.5.1B and compiled into one or more truth statements within a truth table extending from 6.3B for a specific identifier at 6.5B.

At 6.6B a DPE routine may end at 6.7B or may return to polling for available data from aggregators 6.1B if so desired. Data within a diagnostic processing engine will have a limited useful life span assigned to each logic table created including daily, weekly, and monthly. One or more automated tasks will continuously be collecting the information and add/updating related logic rules. Precedence will be determined in reverse order of monthly, weekly, and daily of the logic rules and table for this DPE engine due to changing trends over time.

Figure 7:
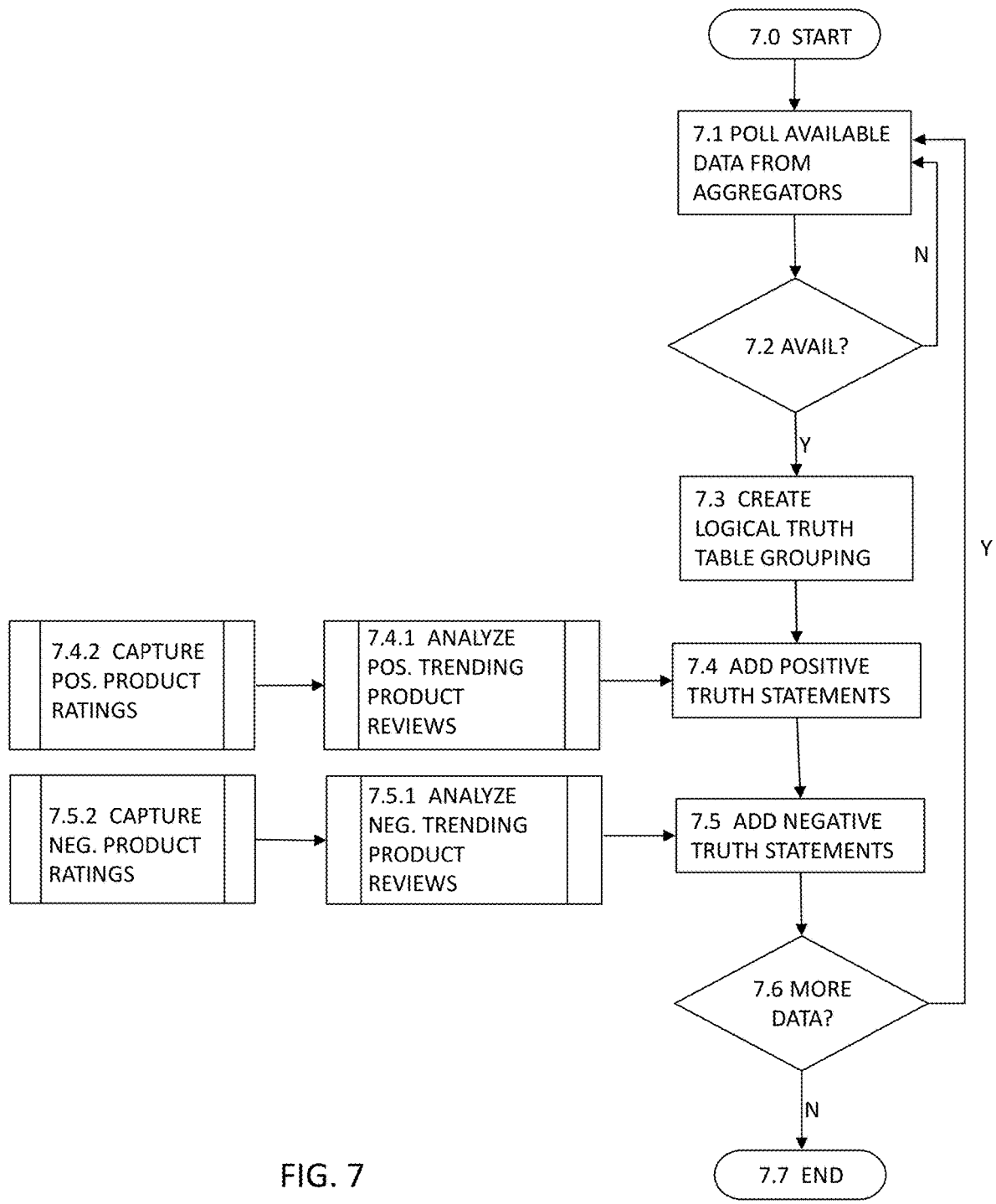
FIG. 7 is an illustration of one embodiment of a method of operation of a product satisfaction engine (PSE).

FIG. 7 is a flowchart illustrating one embodiment of a method of operation of a product satisfaction engine (PSE). A product satisfaction engine one or more of crawls and interfaces with currently available major ecommerce engines, ratings and ranking sites to determine products that are generating positive and negative customer experiences. A PSE utilizes actual product rankings after being standardized to a common scale as well as the total number of experiences across one or more sources to calculate either a positive or negative experience and create one or more of the corresponding logic rules to be added to a DBR knowledge base and processing component.

In this embodiment a method of operation of a PSE starts at step 7.0. At 7.1 a PSE polls available knowledge content from aggregators to determine whether goods have positive or negative rating by consumers, product testers, and other interested parties. Aggregators in the form of one or more of crawlers, bots, and web services will process from their available target source(s) and generate rating results. Target sources may include but are not limited to Google®, MSN®, Yahoo®, Amazon®, EBay®, and others.

Rating data availability is determined at step 7.2. If PSE related data is unavailable, the process loops back to polling at step 7.1 immediately, at a preconfigured time, or at a designated action interval for repeat of step 7.1 until data is captured. Once polled PSE data is available and captured, a check for results that already exist will be performed. If results do not exist, a logical grouping of truth statements is created at step 7.3 in one or more of memory and other computer storage mediums in the form of a truth table having a unique identifier. Truth table responses will be determined based by defined thresholds on key attributes in the current active user population. DBR engine processing performance speed will be enhanced if the PSE truth statements are cached in memory.

Data is also captured when available from one or more of positive product ratings, reviews and feedback 7.4.2 and negative product ratings, reviews and feedback 7.5.2. The captured positive trending product ratings, reviews, and feedback is then analyzed 7.4.1 and added into one or more truth statements within a truth table of 7.3 for a specific identifier 7.4. The captured negative trending product ratings, review, and feedback is then analyzed 7.5.1 and added into one or more truth statements within a truth table of 7.3 for a specific identifier 7.5. At 7.6 a PSE may return to polling for available data from aggregators 7.1 if so desired. Alternatively, the routine may end at 7.7.

Figure 7B:
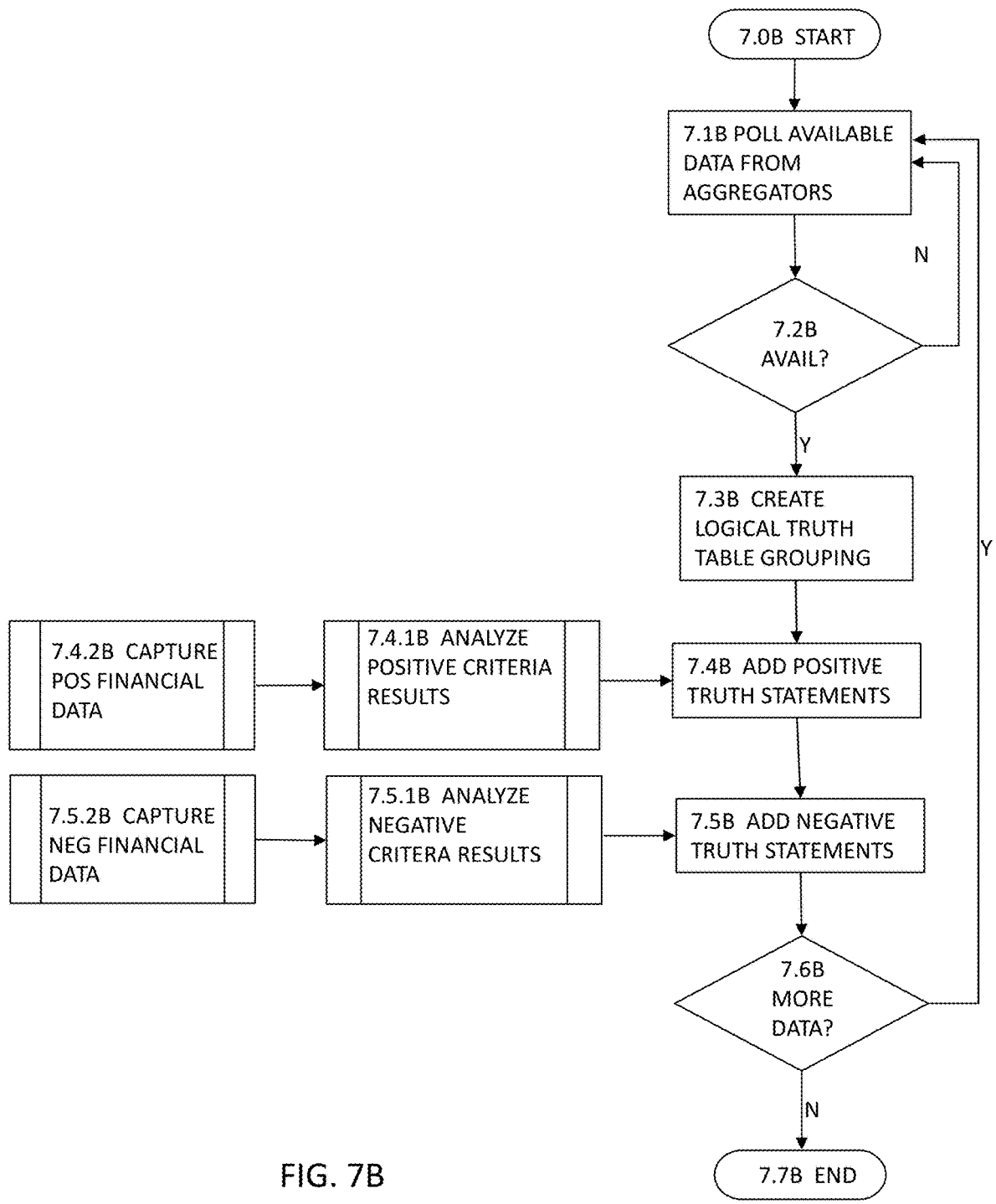
FIG. 7B is an illustration of one embodiment of a method of operation of a financial services engine (FSE).

FIG. 7B is a flowchart illustrating one embodiment of a method of operation of a financial services engine (FSE). A financial services engine processes financial data from one or more financial platforms (sources) to determine if it matches specified criteria. The financial data may include but is not limited to historical and current revenue, profit, loss, cost, and expense detail. It may also include future projections for revenue, profit, loss, cost, and expenses.

In this embodiment a method of operation of a FSE starts at step 7.0B. At 7.1B a FSE polls available financial data from aggregators to determine whether the data has positive or negative criteria results. Aggregators in the form of one or more of crawlers, bots, and web services will process from their available target source(s) and generate results. Target sources may include but are not limited to YAHOO FINANCE, WALL STREET JOURNAL, MOTLEY FOOL, ZACKS INVESTMENT RESEARCH, MORNING STAR, SEEKING ALPHA, and others.

Rating data availability is determined at step 7.2B. If FSE related data is unavailable, the process loops back to polling at step 7.1B immediately, at a preconfigured time, or at a designated action interval for repeat of step 7.1B until data is captured. Once polled FSE data is available and captured, a check for results that already exist will be performed. If results do not exist, a logical grouping of truth statements is created at step 7.3B in one or more of memory and other computer storage mediums in the form of a truth table having a unique identifier. Truth table responses will be determined based by defined thresholds on key attributes in the current active user population. DBR engine processing performance speed will be enhanced if the FSE truth statements are cached in memory.

Data is also captured when available from one or more of positive financial data 7.4.2B and negative financial data 7.5.2B. The captured positive trending financial data is then analyzed 7.4.1B and added into one or more truth statements within a truth table of 7.3B for a specific identifier 7.4B. The captured negative trending financial data is then analyzed 7.5.1B and added into one or more truth statements within a truth table of 7.3B for a specific identifier 7.5B. At 7.6B a FSE may return to polling for available data from aggregators 7.1B if so desired. Alternatively, the routine may end at 7.7B.

Figure 7C:
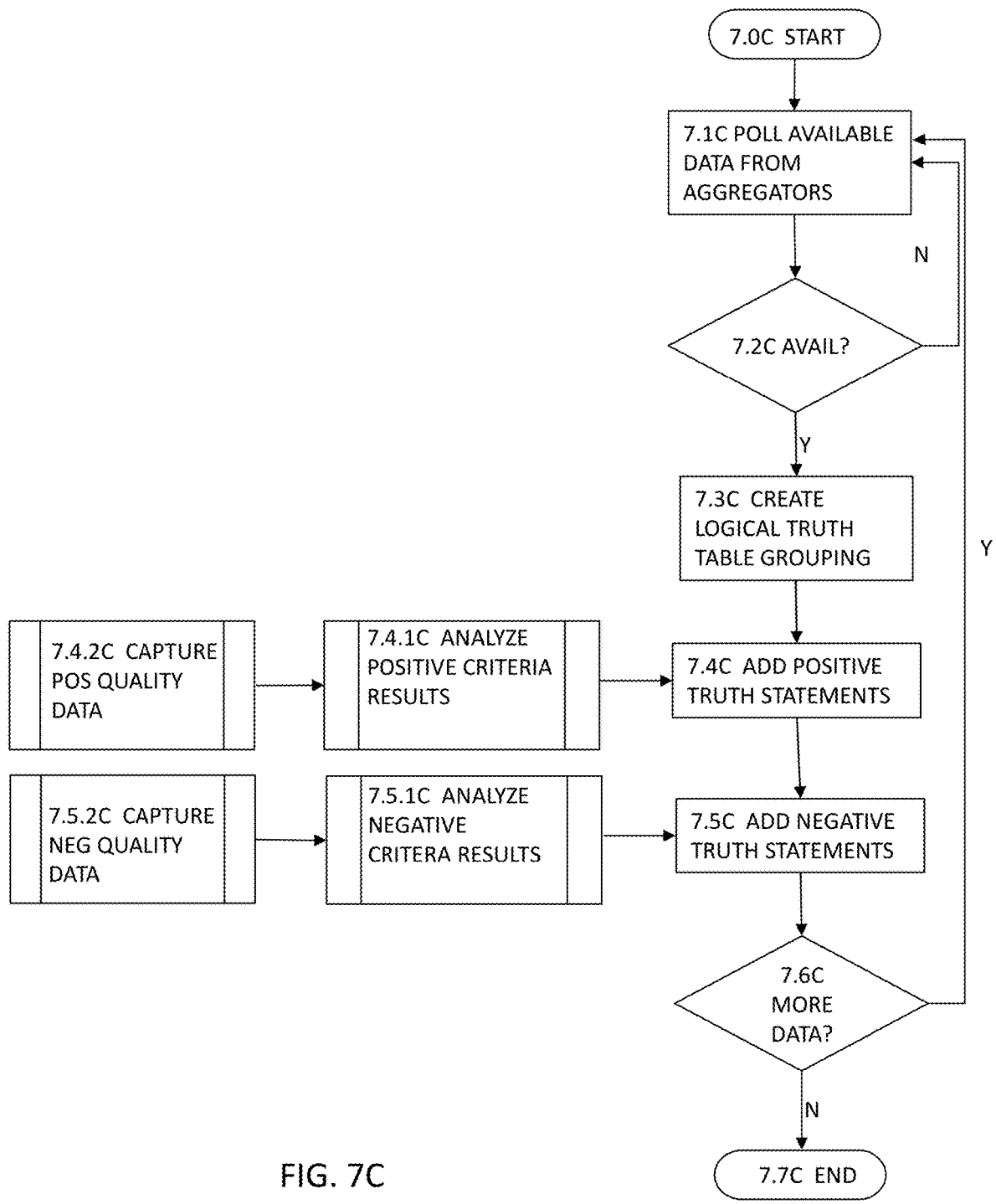
FIG. 7C is an illustration of one embodiment of a method of operation of a quality assurance engine (QAE).

FIG. 7C is a flowchart illustrating one embodiment of a method of operation of a quality assurance engine (QAE). A quality assurance engine processes data from one or more quality devices including but not limited to programmable logic controllers, radio frequency devices, computing devices, robotic devices, and various instrumentation devices. The quality assurance engine supports data in a structured or non-structured format.

In this embodiment, a method of operation of a QAE starts at step 7.0C. At 7.1C a QAE polls available quality data from aggregators to determine whether the data has positive or negative criteria results.

Rating data availability is determined at step 7.2C. If QAE related data is unavailable, the process loops back to polling at step 7.1C immediately, at a preconfigured time, or at a designated action interval for repeat of step 7.1C until data is captured. Once polled QAE data is available and captured, a check for results that already exist will be performed. If results do not exist, a logical grouping of truth statements is created at step 7.3B in one or more of memory and other computer storage mediums in the form of a truth table having a unique identifier. Truth table responses will be determined based by defined thresholds on key attributes in the current active user population. DBR engine processing performance speed will be enhanced if the QAE truth statements are cached in memory.

Data is also captured when available from one or more of positive quality data 7.4.2C and negative quality data 7.5.2C. The captured positive trending quality data is then analyzed 7.4.1C and added into one or more truth statements within a truth table of 7.3C for a specific identifier 7.4C. The captured negative trending quality data is then analyzed 7.5.1C and added into one or more truth statements within a truth table of 7.3C for a specific identifier 7.5C. At 7.6C a QAE may return to polling for available data from aggregators 7.1C if so desired. Alternatively, the routine may end at 7.7C.

Figure 8:
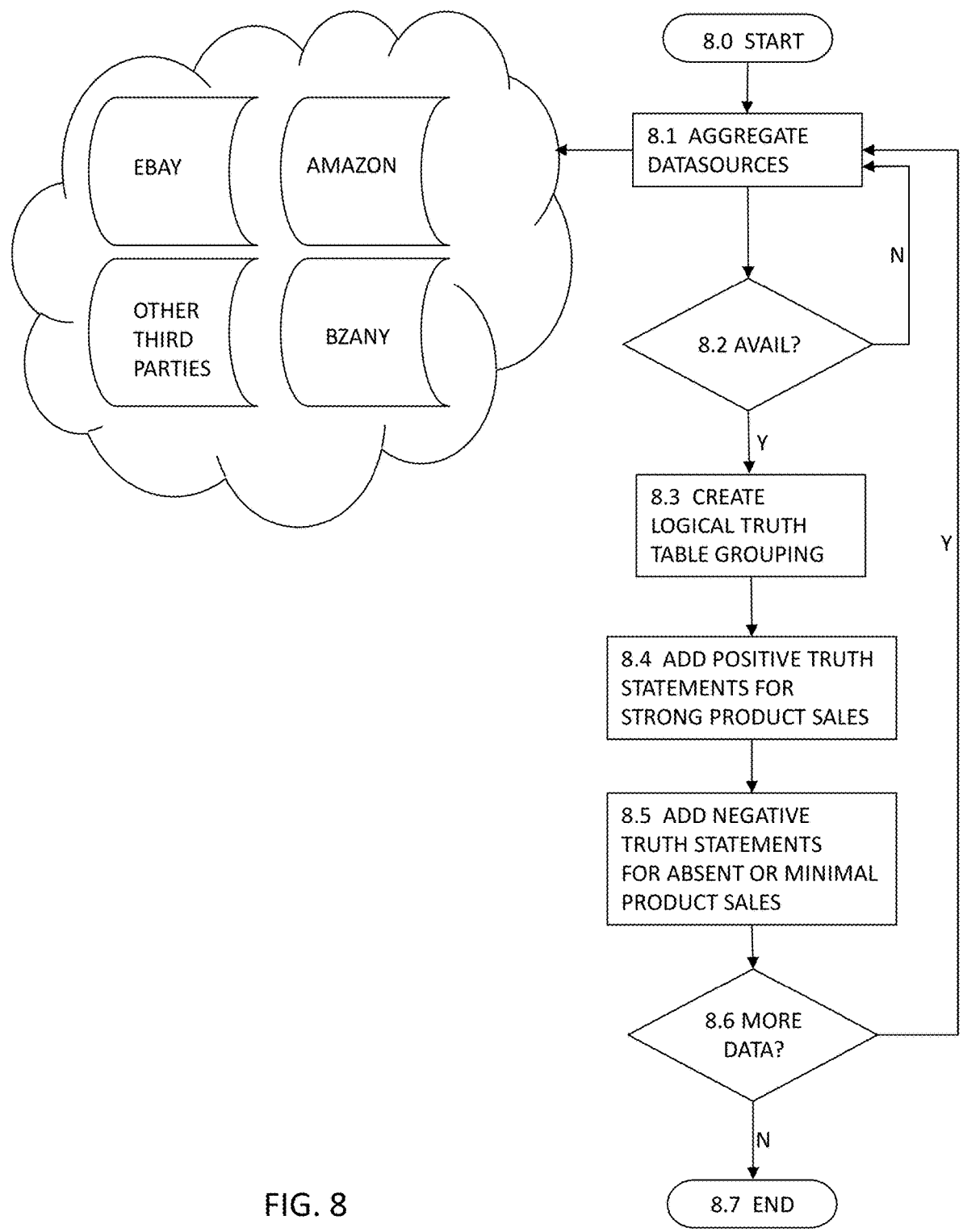
FIG. 8 is an illustration of one embodiment of a method of operation of a sales history engine of all consumers (SHE)

FIG. 8 is a flowchart illustrating one embodiment of a method of operation of a sales history engine (SHE) starting at step 8.0. A sales history engine uses sales history data to determine popularity for a given time period of one or more goods that may be used to create a configured package. Data for a sales history engine is polled from one or more internal and external aggregate data sources (crawlers, bots, web service). The SHE then generates results when the data is available. FIG. 8 is an illustrative example of an aggregation of data regarding sales history for specified goods at Ebay®, Amazon®, Bzany®, and other third parties such as Walmart® and Zulily®. If sales history data is available, the data is processed. When sales history data is unavailable, the SHE routine loops back to step 8.1 where a SHE will continue to poll available knowledge content from aggregators immediately, at a configured time, or at a predetermined action interval. When sales history data is available, aggregated data is used to create logical truth table groupings at step 8.3. If sales history data does not already exist a logical grouping of truth statements with a unique identifier is created in one or more of memory, disk, and a storage portion of an associated computing device. Caching the information in memory will provide optimal performance for DBR processing.

A high count of successfully completed purchases on a particular item would be deemed as positive (true) and a logic rule would be added for a DBR component at step 8.4. A low count of sales on a particular good would be deemed as negative (false) and creation of one or more logic rules is added to a DBR knowledge base and processing component at step 8.5. Sales history goods in preferred embodiments are identified by UPC or GTIN. At this point, a SHE may loop back to poll available knowledge content from aggregators as described in step 8.1. If additional inventory data is unnecessary, SHE routines may end at 8.7.

Figure 9:
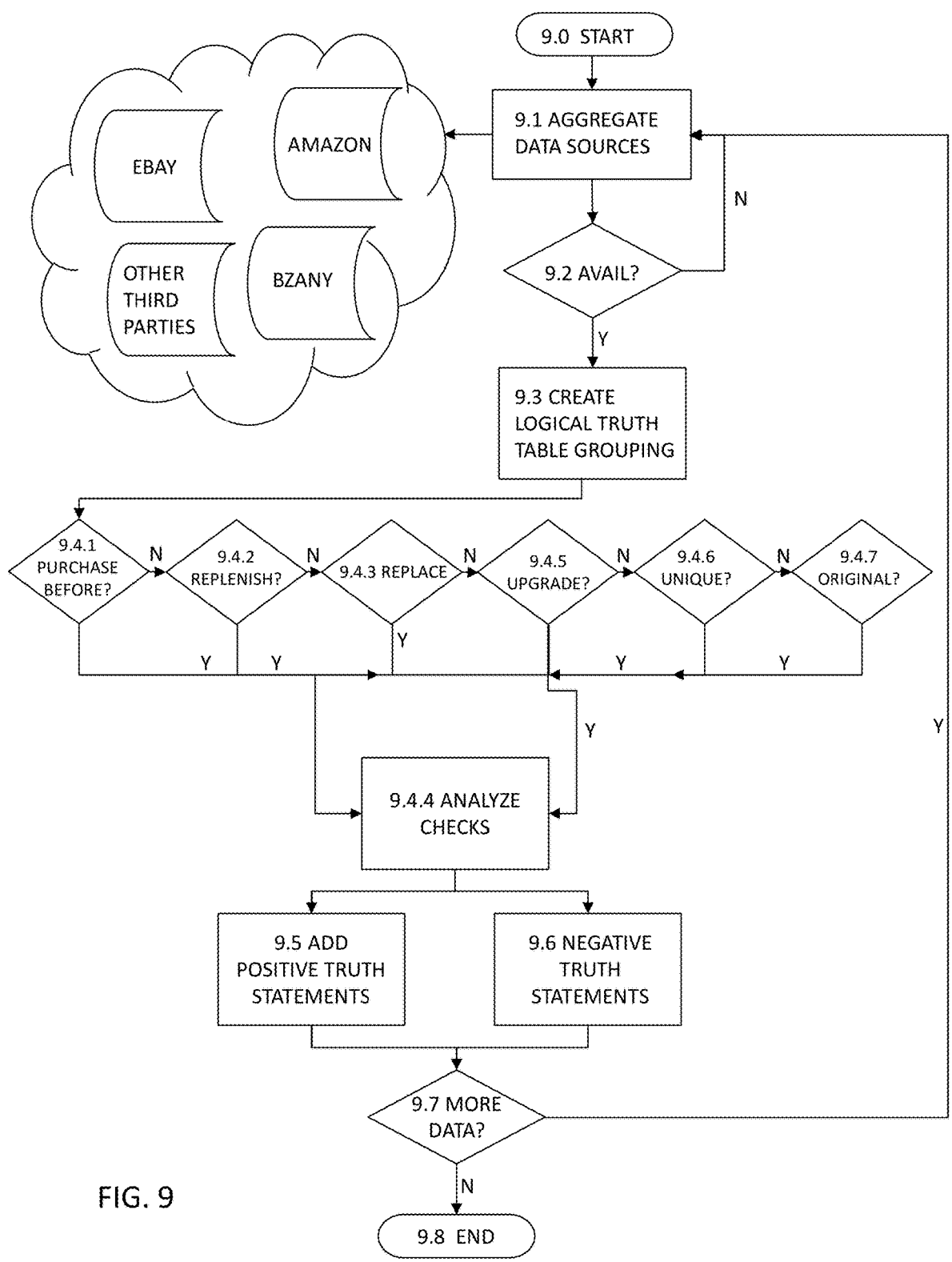
FIG. 9 is an illustration of one embodiment of a method of operation of a customer purchase history engine (CPH)

FIG. 9 is a flowchart illustrating one embodiment of a method of operation of a customer purchase history (CPH) starting at step 9.0. A customer purchase history engine uses customer purchase history from a customer on a current visit and any optionally saved previous visits to determine a customer's preferred brands, themes, and interests for one or more goods that may be used to create a configured package. Data for a customer purchase history engine is polled from one or more internal and external aggregate data sources (crawlers, bots, web service). The CPH then generates results when the data is available. FIG. 9 is an illustrative example of an aggregation of data regarding customer purchase history for specified goods at Ebay®, Amazon®, Bzany®, and other third parties such as Walmart® and Zulily®. If customer purchase history data is available, the data is processed. When customer purchase history data is unavailable, the CPH routine loops back to step 9.1 where a CPH engine will continue to poll available knowledge content from aggregators immediately, at a configured time, or at a predetermined action interval. When customer purchase history data is available, aggregated data is used to create logical truth table groupings at step 9.3. If customer purchase history data does not already exist a logical grouping of truth statements with a unique identifier is created in one or more of memory, disk, and a storage portion of an associated computing device. Caching the information in memory will provide optimal performance for DBR processing.

A CPH engine provides a DBR engine information to identify preferred customer brands, themes and interests for a customer. One or more checks may be performed on collected purchase history information from one or more aggregate data sources 9.1. An affirmative customer purchase history using factors illustrated in (9.4.1-9.4.7) would be deemed as true, whereas non-affirming customer purchase history using these same factors would be deemed as false. Examples of CPH checks include determining if; a product has been purchased previously 9.4.1, a product is a replenishment or a new purchase (i.e. razor blades) 9.4.2, a product is replacing an existing product (i.e. TV), a product to upgrade an existing product (i.e. laptop), a product that is a one of a kind item (i.e. antique), and a product that is an original item (i.e. art). Additional checks may be added to improve mapping. Analysis of checks data 9.4.1-9.4.7 is then completed 9.4.4. Information from the checks and aggregate data sources is used to generate a portion of the logic rules and dynamic weightings for a DBR knowledge base and processing component. A high count of successfully completed customer purchases on a particular item would be deemed as positive (true) and a logic rule would be added for a DBR component at step 9.5. A low count of customer purchase sales on a particular good would be deemed as negative (false) and creation of one or more logic rules is added to a DBR knowledge base and processing component at step 9.6. Customer purchase history goods in preferred embodiments are identified by UPC or GTIN. At this point, a CPH routine may loop back to poll available knowledge content from aggregators as described in step 9.1. If additional customer purchase data is unnecessary, CPH routines may end at 9.8.

Figure 10:
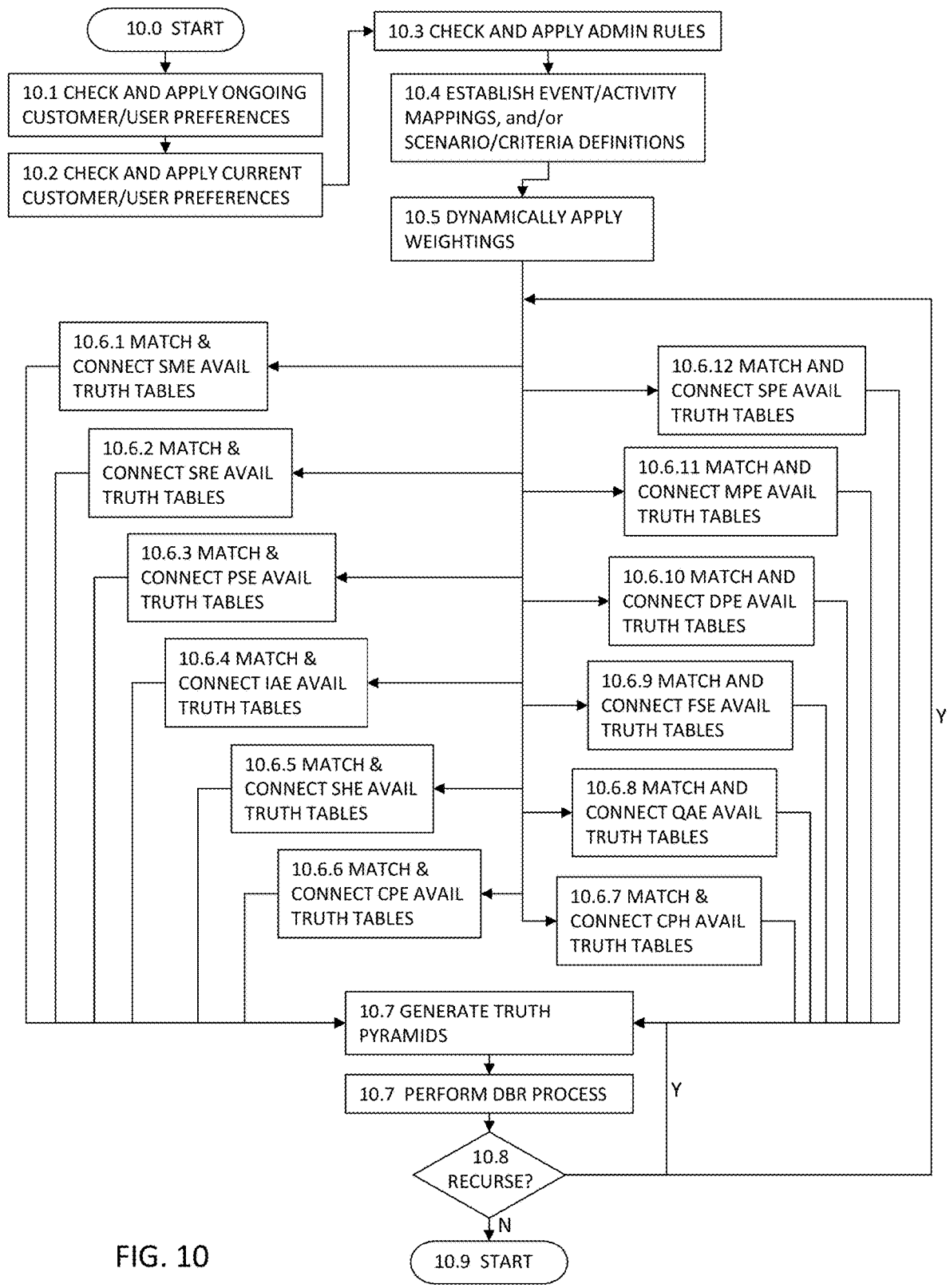
FIG. 10 is an illustration of one embodiment of a method for operation of a determine best results engine (DBR)

FIG. 10 is a flowchart illustrating one embodiment of a method of operation of a determine best results engine (DBR). A DBR processes three or more knowledge bases that stores one or more logic rules for one or more of: individual product items, services, and results, that make up at least one of a configured package of one or more goods, services, and results (GSR). A DBR processing component uses knowledge bases of contributing engines and logic rules within the knowledge bases to determine best possible matches for resulting items within configured packages based on inputs from contributing engines (CPE, SME, SRE, SHE, IAE, PSE, ADR, CPH, SPE, MPE, DPE, FSE, QAE, etc.). Each contributing engine will create and share truth tables for its specific functional area to a DBR engine.

FIG. 10 illustrates one embodiment of a method of operation of a DBR engine. In this embodiment, a DBR engine starts 10.0 by checking and applying historical customer/user preferences 10.1 then checking and applying current selected customer/user preferences 10.2. For configured packages of products and/or services for example, these customer preferences can include event selection, theme selection, style/color selection, and other event details from instant customer input into a computing device linked to a determine best result web service system. For a configured package of results for example, these user preferences can include scenario selection, element selection, criteria selection, and various rules. The associated DBR engine then checks events and configuration packages (or results) available to these selections and other administrative defined rules 10.3 to establish event and activity mappings 10.4. For results, the associated DBR engine then checks configuration packages available to these scenarios and criteria. Dynamic weighting is then applied to each mapping 10.5. At 10.6.1-10.6.12, truth tables from each contributing knowledge engine are matched and connected to the most recently generated DBR truth table. One or more truth pyramids are generated 10.7 based on criteria and ranges established in 10.1-10.5. The DBR engine generates truth pyramids and processes the data contained therein 10.7. The system recurses 10.8 as illustrated until a DBR calculation is fulfilled. One or more best configured packages containing one or more of goods, services, and results is then presented to the customer engaging the determine best package web system. The DBR routine may end at 10.9.

Figure 11:
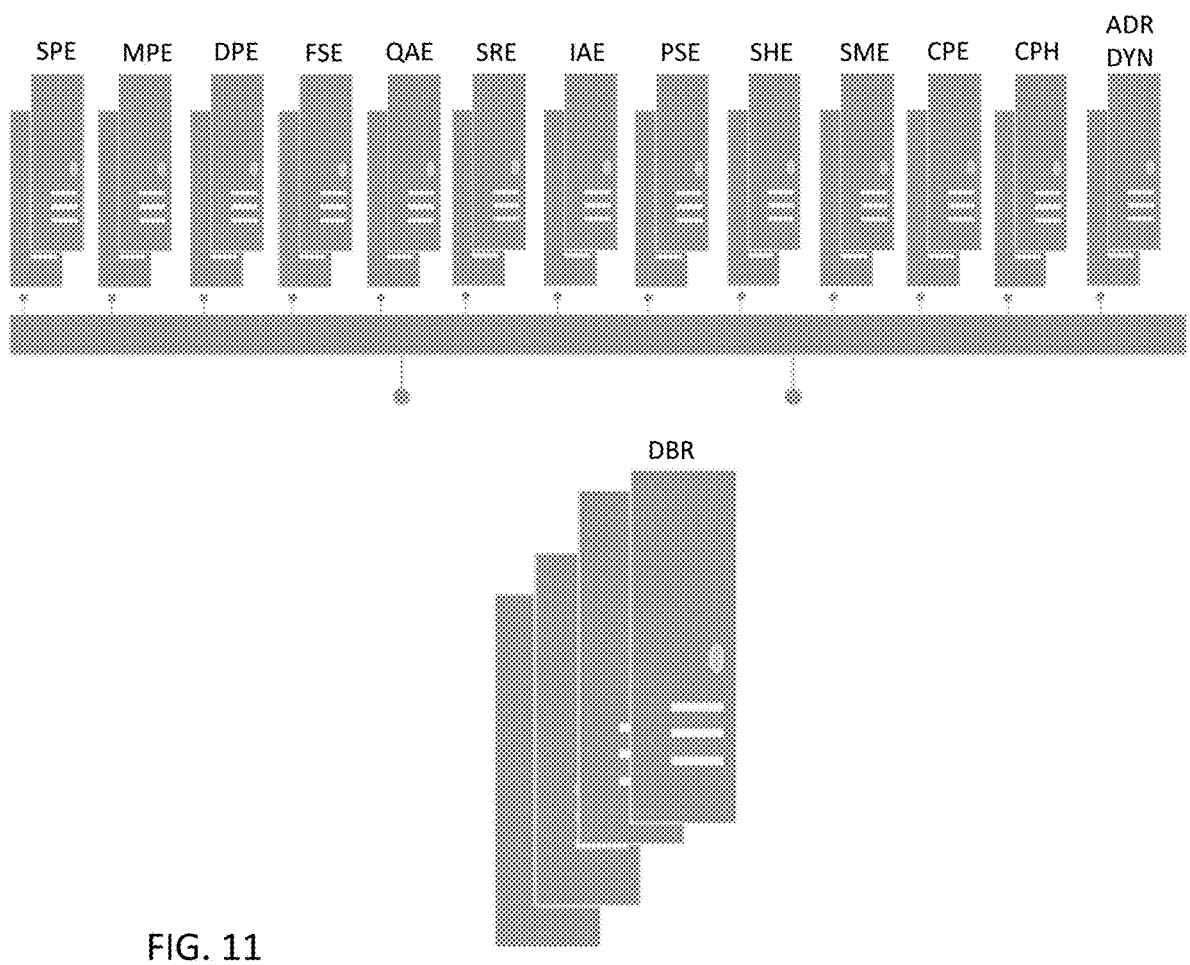
FIG. 11 is an illustration of one embodiment of a plurality of data knowledge engines and a determine best result engine sharing data through a cloud.
Figure 12:
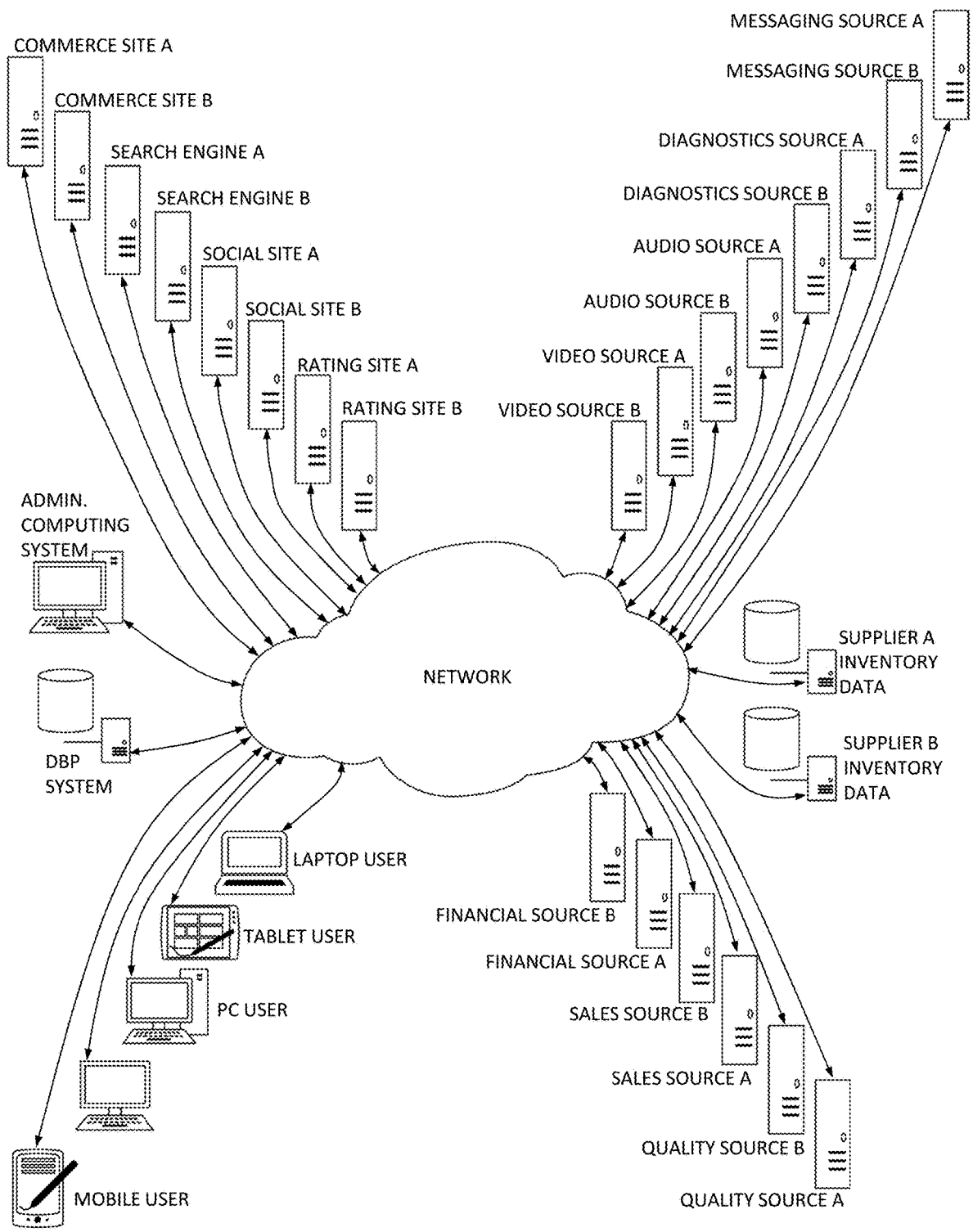
FIG. 12 is a diagram illustrating one embodiment of a determine best package web service system with various contributing knowledge engines operating in a cloud and also illustrating various types of computing devices that may be used by customers and administrators to access a system.

FIG. 12 is a diagram illustrating one embodiment of a determine best package web service system with various data engines operating over a network and also illustrating various types of computing devices that may be used by customers, users, and administrators to interact and perform various computing procedures with a determine best package web service system. In some embodiments, the network is in the form of a cloud. Computing devices may include any of a wide variety of computing devices including one or more of a desktop computer, a notebook or laptop computer, a server computer, a smart phone, a mobile or handheld computer, and a tablet computer. Computing devices can function as a server, a client, or any other computing entity. Computing devices within a determine best package web service system can perform various monitoring functions as discussed herein and can execute one or more application programs, such as application programs described herein. Data engines within a determine best package (DBP) web service system may interact over a network while receiving input and output from various computing devices. A determine best package system can include one or more administrator terminals for managing administrator facing features of the system. As illustrated in FIG. 12, one or more of the data engines or computing devices may include storage devices (illustrated as cans). FIG. 11 is an illustration of one embodiment of a plurality of data knowledge engines and a determine best result engine sharing data through a cloud.

As illustrated by example and not limitation in FIG. 13, computing components interfacing with a DBP web service system may include one or more processor(s), one or more memory device(s), one or more interface(s), one or more local or remote mass storage device(s), one or more of Input/Output (I/O) device(s) such as a mouse and keyboard and voice recognition and video and touch device, and one or more display, all of which are coupled to a bus. Processor(s) include one or more processors and controllers that execute instructions stored in memory device(s) and mass storage device(s). Processor(s) may also include various types of computer-readable media, such as cache memory.

In one embodiment, a web service system provides planning and automatic configuration of an array of one or more of goods and services that a user will need for a party, task, or other event being planned. In other embodiments, a web service system provides a configured package of results useful in industries such as manufacturing, medical, and financial services. A web service system comprises administrator facing features and consumer facing features. As illustrated in the embodiment of FIG. 14, administrator facing features include package maintenance, event maintenance, and package to event maintenance modules. Each of these are editable by an administrator through an administrator computing device in communication with the web service system and provide the administrator a tool for defining relationships between packages, events, and goods or services that will be provided by the web service system. Likewise, and as illustrated in FIG. 14B, the administrator computing device can be used to communicate with the web service system to define rules, scenarios and criteria required for a configured package of results.

FIGS. 15 and 16 illustrate an example of screens an administrator may utilize to add a package of products available for the consumer to choose from in the consumer facing portion of the program (FIG. 15) and then to maintain a package (FIG. 16) for the online commerce sector. Here an administrator chooses a package ID, assigns a package name, and sets an optional start date and end date for when the package will be available as a choice for the consumer. A status option provides the administrator the option to set the status of the package to 'Active' making the package visible to the consumer or 'Inactive' to hide the package from consumer view. The package is maintained by choosing one of the available packages then choosing from available package items for inclusion or removal from the package using the arrow buttons and clicking OK to confirm the choices or Cancel to exit.

FIG. 17 illustrates an example of a screen an administrator may utilize to add events such as a child's birthday or a retirement to a list of choices a consumer may choose from for the online commerce sector. An event ID is chosen and an event name is assigned in an event name box. A start and end date for when an event will be available as a choice for the consumer is chosen. A status option provides the administrator the option to set the status of the event to 'Active' making the package visible to the consumer or 'Inactive' to hide the package from consumer view. Clicking OK confirms the choice.

FIG. 18 illustrates an example of a screen an administrator may utilize to easily select package(s) for linking to each event type for the online commerce sector. Multiple packages can belong to each event type. The administrator first selects or searches for an event in the system using the provided dialog boxes. Once an event is identified, a configuration package of goods assigned to the specified event is illustrated in the assigned packages window. These are the packages that will be visible to the consumer in the consumer facing portion. Available packages are viewable in the available packages window. The arrow buttons are used to add or remove packages from an assigned packages window. Additional packages can be searched from a search packages window box and pressing go. Clicking OK confirms the package to event linking.

Figure 19:
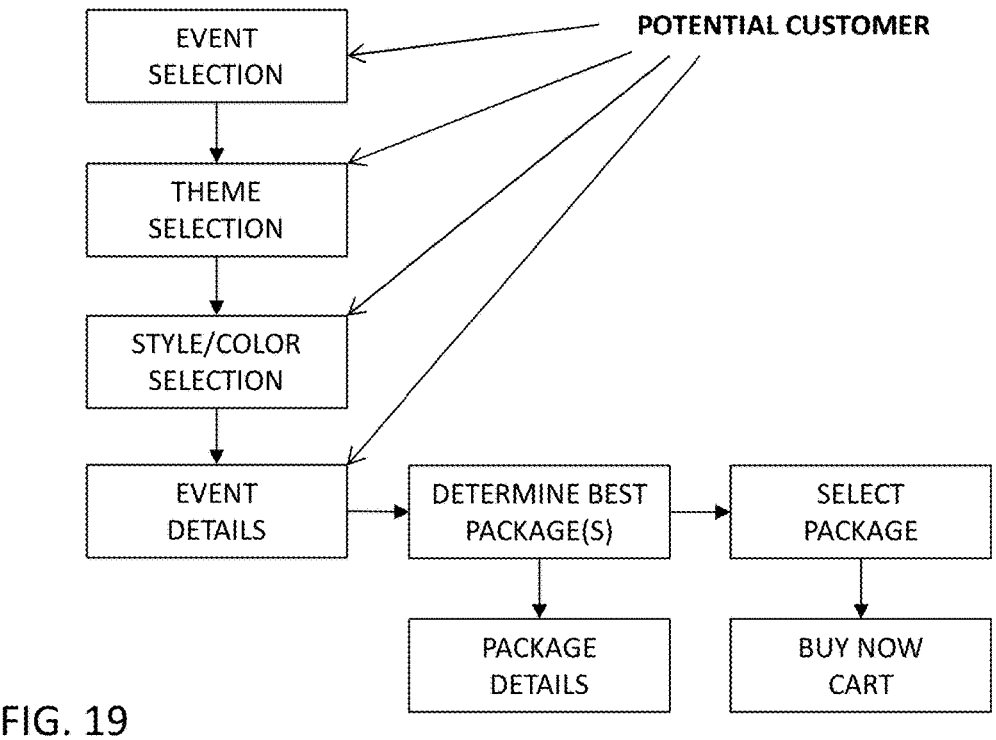
FIG. 19 illustrates one embodiment of a method a potential customer of a web service system will utilize from choosing an event in the system to placing the selected package in an ecommerce shopping cart.

FIG. 19 illustrates an example of a process of online event planning from the perspective of features of the system utilized by a customer (consumer) for the online commerce sector. It is preferred that the consumer facing feature uses a step-by-step 'wizard' for consumer use to ultimately provide the consumer with a recommended list (configuration) of items needed for their event. Utilizing the online system from their computing device, the consumer first selects an event, then a theme, then a style or color. The customer then adds details about the event to the system. The web service system then provides the user with the choice of several packages suitable to meet the consumer's preferences. The consumer then selects one or more packages of goods available online and adds the package(s) to their buy cart before checking out. The available packages may be compiled with input from a DBR engine that compiles and analyzes data from a variety of knowledge engines.

Figure 19B:
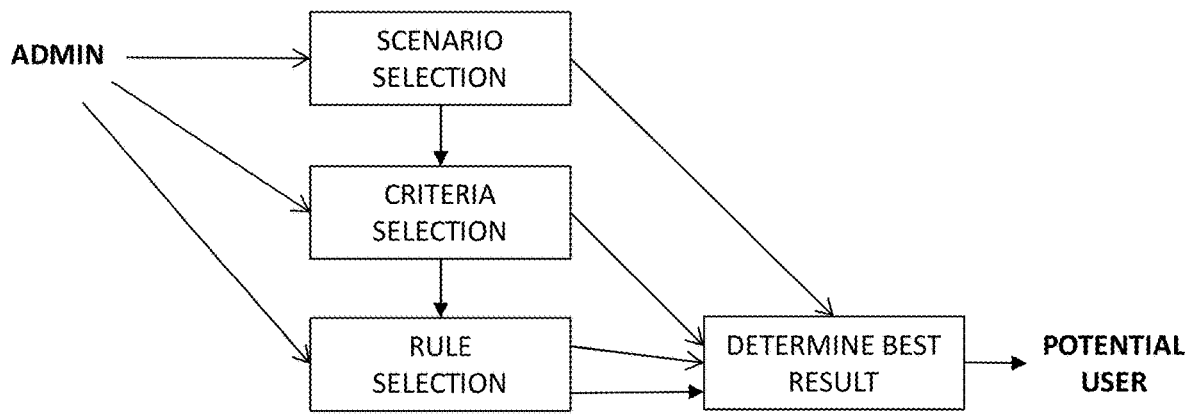
FIG. 19B illustrates one embodiment of a method for a web service system administrator to select scenarios, criteria, and rules and for a potential user to interface with a DBR.

FIG. 19B illustrates an example of selections in a web service system much like the one described in FIG. 19. The system of FIG. 19 utilizes a determine best result engine to determine a best package of products in response to the selection of an event, theme, style/color, and other event details. The system of FIG. 19B on the other hand, is directed to utilizing a determine best result engine to determine a best result based selection of a scenario, criteria, and one or more rules established by an administrator. In this context, and depending on the nature of the result determined by the determine best result engine, a 'package' can alternatively be described as a 'scenario', a 'product' alternatively described as an 'element', a 'theme' alternatively described as a 'rule', and 'color' alternatively described as yet another 'rule'. Similarly, at least one 'product' is in a package just as one or more 'elements' are in a scenario. Further, just as 'packages' are mapped to 'events', 'scenarios' are mapped to 'criteria'. Similarly, just as at least one rule is applied to a 'package', at least one rule is applied to a 'scenario'. These points are further illustrated in FIG. 19C whereby the webservice system utilizes a determine best result engine to determine the best result not only in the online commerce sector, but also in the manufacturing sector, healthcare sector, and financial sector. FIG. 19C represents only one of countless examples of how the determine best result engine in a web service system analyzes and compiles data from any variety of knowledge engines to present a best result.

Note in FIG. 19C an example of a determine best result web service system being used to compile a best result package of products based on data collected from knowledge engines such as a social media engine, a search results engine, and inventory availability engine, and a product satisfaction engine. Further in FIG. 19C, M1 is an example of a determine best result web service system being used in a manufacturing environment to determine a 'scenario' which in this case is a grouping of quality results from a set of machines A, B, C (elements). A 'criteria' is chosen which in this example is a date, with a first rule being a the machines must complete a minimum of 1000 operations/hour. A second rule based on part variance measurement data from a PLC (programmable logic controller) states this variance must be zero or greater and less than 0.17. In this example, data from a messaging knowledge engine, a diagnostics engine, and a quality assurance engine are utilized by the DBR to determine the best result. Likewise, M2 is another example. In this case, the elements are machine D, E and F with a first rule again related to the part variance data from a PLC as noted previously. A second 'rule' states the parts must not have dependences on parts created during M1. In this example, data from a messaging knowledge engine, a diagnostics engine, and quality assurance engine are utilized by the DBR to determine the best result.

In a healthcare environment, FIG. 19C illustrates H1 which in this 'scenario' is a grouping of vaccine candidates. The 'element' is a trial vaccine A, B and C. The 'criteria' is set to a trial period between March and June of 2020. In this example, a streaming engine, a messaging engine, and a product satisfaction engine provide data to a DBR engine to determine a best result of vaccines. FIG. 19C also illustrates H2 which in this 'scenario' is a grouping of test patient candidates. The element is a patient trial group A, B and C. The 'criteria' is set to a positive reaction type that in a first rule excludes the top 3% and in a second rule all are linked to vaccine A. In this example, a streaming engine, a messaging engine, a diagnostics engine, and a quality assurance engine provide data to a DBR engine to determine a best result of the patient trial. FIG. 19C also illustrates H3 which in this 'scenario' is a grouping of test patient candidates. The element is a patient trial group A, B and C. The 'criteria' is set to a negative reaction type that in a first rule excludes the bottom 3% and in a second rule all are linked to vaccine B. In this example, a streaming engine, a messaging engine, a diagnostics engine, and a quality assurance engine again provide data to a DBR engine to determine a best result of the patient trial.

In a financial environment, FIG. 19C illustrates F1 which in this 'scenario' is a grouping of "green stocks". The 'element' is a stock group A, B, and C. The 'criteria' is set as a month over month analysis. A first 'rule' is a greater than 5% ROI (return on investment) and a second 'rule' is that the stocks cannot be considered a traditional energy stock. In this example, a financial services engine, a messaging engine, a social media engine, and a search results engine are utilized to provide data to a DBR engine to determine a best result of a grouping of green stocks. FIG. 19C also illustrates F2 which in this 'scenario' is also a grouping of "green stocks". The 'element' is a stock group D, E, and F. The 'criteria' is set as a month over month analysis. A first 'rule' is a greater than 5% loss and a second 'rule' is that the stocks cannot have a relationship with any stock in the F1 grouping. In this example, a financial services engine, a messaging engine, a social media engine, and a search results engine are utilized to provide data to a DBR engine to determine a best result of a grouping of green stocks.

Figure 20:
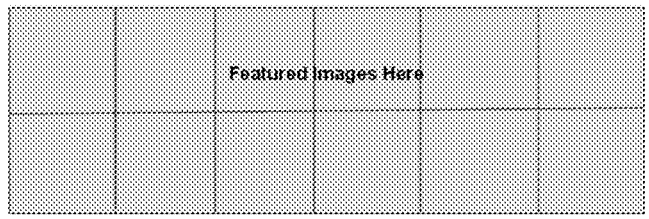
FIG. 20 illustrates one embodiment of an image displayed by a screen of a computing device providing event selection choices to enable a customer to choose an event available in a web service system.

FIG. 20 illustrates an example of a screen a consumer may utilize to select an event for the online commerce sector. Using the dialog boxes available, the consumer chooses from available events or searches for a desired event using an event search box and Go button. Alternatively, a user may search for featured events by image icons representing an event such as a birthday or anniversary. Once a desired event is found, it is highlighted by the consumer before advancing to an event theme screen. The previous and next buttons assist the consumer in moving to the next screen (i.e. theme selection, or a previous screen.

Figure 21:
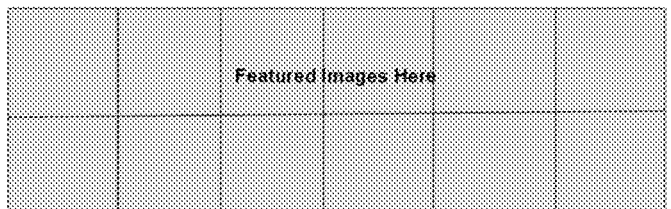
FIG. 21 illustrates one embodiment of an image displayed by a screen of a computing device providing theme selection choices to enable a customer to choose a theme available in a web service system.

FIG. 21 illustrates an example of a screen a consumer may utilize to select an event theme for the online commerce sector. Operating much like the event selection dialog box, the user chooses from a drop-down list or searches for a desired theme. Once a desired theme is found, it is highlighted by the consumer before advancing to an event style or color screen.

Figure 22:
FIG. 22 illustrates one embodiment of an image displayed by a screen of a computing device providing one or more of style and color selection choices to enable a customer to choose a corresponding style and color available in a web service system.

FIG. 22 illustrates an example of a screen a consumer may utilize to select a style or color for an event for the online commerce sector. Again, operating much like an event selection dialog box, a user chooses from a drop-down list or searches for a desired style or color. Once a desired style or color is found, it is highlighted by the consumer before advancing to an event details screen.

FIG. 23 illustrates an example of a screen a consumer may utilize to input event details for the online commerce sector. Dialog boxes are present for a consumer to key in the number of attendees and number of tables. In addition, drop down lists allow a user to choose the size of tables, shape of tables, and any other criteria pertinent to an event plan such as child or adult event. Clear, save, and cancel buttons are available to clear the selections, save, or cancel them. After completion of the event details page, the consumer is then presented with pre-configured packages of goods meeting the specifications of the consumer's event. Included is pricing for each package and a 'buy now' option to insert the items into the online shopping cart for purchase. In preferred embodiments, the packages available to the consumer include results from a determine best result engine.

FIG. 24 illustrates one embodiment of an image displayed by a screen of a consumer's computing device providing one or more recommended packages as a result of a web service system for the online commerce sector. In this embodiment, each package may be represented by an icon in a featured images section. The screen also displays a review of details of customer inputs here illustrated as # of attendees, # of tables, size of tables, shape of tables, etc. In a results portion of the screen, a total price is displayed which may include a price per attendee. A clickable button to buy a chosen configured package is included. The configured package(s) may be saved by clicking a save button.

It is noted that the terms "substantially" and "about" and "generally" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

The foregoing invention has been described in accordance with the relevant legal standards, thus the description is exemplary rather than limiting in nature. Variations and modifications to the disclosed embodiment may become apparent to those skilled in the art and fall within the scope of the invention.

The invention claimed is:

1. A method performed by one or more computing devices of a web service system facilitating users to select a configured package of results comprising the steps of:

saving, on one or more storage portions of said one or more computing devices of said web service system, a product-element table referencing one or more of products, services, and results;

saving, on one or more storage portions of said one or more computing devices of said web service system, one or more configured packages of products, services, and results available from said product-element table;

saving, on one or more storage portions of said one or more computing devices of said web service system, a plurality of selections representing various types of scenarios from which one or more users may choose;

saving, on one or more storage portions of said one or more computing devices of said web service system, one or more configured packages matched to the plurality of selections;

displaying consumer facing options on a client system of a first user;

in response to displaying consumer facing options, receiving, from the first user through the client system of the first user, selections of the consumer facing options;

collecting knowledge data from a plurality of contributing knowledge engines into a determine best results engine whereas the determine best result engine filters out from output of the determine best results engine at least one of: a truth statement and a truth table;

utilizing the knowledge data from the plurality of contributing knowledge data engines to generate one or more intelligent configured packages of results corresponding to consumer facing option selections received by said first user;

displaying on the client system of the first user, said one or more intelligent configured packages of results;

receiving from the first user instructions for one or more of: processing a sale and saving information input by the first user; and activating a computer processor of said web service system to execute said instructions from the first user.

2. The method of claim 1 further comprising the step of the determine best result engine filtering out one or more of: an irrelevant result, an obsolete result, and an erroneous result, for a specific knowledge area represented by each contributing knowledge engine.

3. The method of claim 1 further comprising the step of dynamically applying truth tables to perform knowledge consolidations from contributing knowledge engines.

4. The method of claim 3 further comprising the step of reducing truth statements by use of a pyramid methodology wherein one or more nested truth table is used to calculate final results for each item of a package and an overall configured package.

5. The method of claim 1 further comprising the step of the determine best result engine growing in intelligence over time as it considers larger amounts of data from contributing knowledge engines.

6. The method of claim 1 further comprising the step of collecting data from a plurality of contributing knowledge engines into a determine best results engine whereas the determine best result engine filters out at least one of: a truth statement and a truth table.

7. The method of claim 1 further comprising the step of utilizing information from at least three of the following contributing knowledge data engines to generate the intelligent configured package: a customer preferences engine, a customer's purchase history engine, a sales history of all consumer's engine, a product satisfaction record engine, an inventory availability engine, a current trends on social media engine, and a search engine statistical results engine.

8. The method of claim 1 further comprising the step of utilizing information from any plurality of the following contributing knowledge data engines to generate the intelligent configured package: a streaming processing engine, a messaging processing engine, a diagnostics engine, a financial services engine, and a quality assurance engine.

9. The method of claim 1 further comprising the step of utilizing information from any plurality of the following contributing knowledge data engines to generate the intelligent configured package: a streaming processing engine, a messaging processing engine, a diagnostics engine, a financial services engine, a quality assurance engine, a customer preferences engine, a customer's purchase history engine, a sales history of all consumer's engine, a product satisfaction record engine, an inventory availability engine, a current trends on social media engine, and a search engine statistical results engine.

10. The method of claim 1 further comprising the step of selecting a grouping of vaccine candidates as one scenario from the consumer facing options.

11. The method of claim 1 further comprising the step of selecting a grouping of test patient candidates as one scenario from the consumer facing options.

12. The method of claim 1 further comprising the step of selecting a grouping of stocks as one scenario from the consumer facing options.

13. The method of claim 1 further comprising the step of selecting a grouping of quality results from a set of machines as one scenario from the consumer facing options.

14. The method of claim 1 further comprising the step of selecting at least one of a positive and a negative reaction type as one criteria from the consumer facing options in a vaccine trial.

15. The method of claim 1 further comprising the step of selecting a month over month analysis as one criteria from the consumer facing options.

16. The method of claim 1 further comprising the step of selecting from the consumer facing options a part variance rule based on part variance measurement data from at least one of a machine's programmable logic controller and a computing device.

17. The method of claim 1 further comprising the step of selecting from the consumer facing options a return on investment rule based on the historic return on investment of a stock.

18. The method of claim 1 further comprising the step of selecting a trial period date range as one criteria from the consumer facing options.

19. The method of claim 1 further comprising the step of a determine best result engine utilizing data from at least a diagnostics engine and a quality assurance engine.

20. The method of claim 1 further comprising the step of selecting a minimum operations per hour rule for a machine from the consumer facing options.

21. The method of claim 1 further comprising the step of selecting a specific no relationship between scenarios as one rule from the consumer facing options.

22. The method of claim 1 further comprising the step of selecting a specific relationship between scenarios as one rule from the consumer facing options.

* * * * *